United States Patent
Robertson et al.

(10) Patent No.: US 8,722,339 B2
(45) Date of Patent: May 13, 2014

(54) IMMUNOASSAY METHODS

(75) Inventors: John Forsyth Russell Robertson, Nottingham (GB); Anthony Barnes, Dunwoody, GA (US); Andrea Murray, Leicesterschier (GB); Caroline Chapman, Leicesterschier (GB)

(73) Assignee: Oncimmune Ltd., Nottingham (GB)

( * ) Notice: Subject to any disclaimer, the term of this patent is extended or adjusted under 35 U.S.C. 154(b) by 954 days.

(21) Appl. No.: 11/814,516

(22) PCT Filed: May 26, 2006

(86) PCT No.: PCT/GB2006/001944
§ 371 (c)(1),
(2), (4) Date: Aug. 20, 2008

(87) PCT Pub. No.: WO2006/126008
PCT Pub. Date: Nov. 30, 2006

(65) Prior Publication Data
US 2008/0305476 A1  Dec. 11, 2008

Related U.S. Application Data

(60) Provisional application No. 60/685,422, filed on May 27, 2005.

(30) Foreign Application Priority Data

May 27, 2005 (GB) .................................. 0510943.4

(51) Int. Cl.
*G01N 33/53* (2006.01)
(52) U.S. Cl.
USPC ......................................................... 435/7.1
(58) Field of Classification Search
None
See application file for complete search history.

(56) References Cited

U.S. PATENT DOCUMENTS

| | | | |
|---|---|---|---|
| 4,898,951 | A | 2/1990 | Symons |
| 4,937,185 | A | 6/1990 | Webb et al. |
| 5,157,020 | A | 10/1992 | Kay et al. |
| 5,501,955 | A | 3/1996 | Bergman |
| 5,561,049 | A | 10/1996 | Vold et al. |
| 5,652,115 | A | 7/1997 | Marks et al. |
| 5,721,105 | A | 2/1998 | Bergmann |
| 5,726,023 | A | 3/1998 | Cheever et al. |
| 5,747,268 | A | 5/1998 | Herring et al. |
| 5,763,164 | A | 6/1998 | Calenoff |
| 5,827,666 | A | 10/1998 | Finn et al. |
| 5,876,728 | A | 3/1999 | Kass et al. |
| 5,885,793 | A | 3/1999 | Griffiths et al. |
| 6,187,306 | B1 | 2/2001 | Pardoll et al. |
| 6,280,962 | B1 | 8/2001 | Cohen |
| 6,322,989 | B1 | 11/2001 | Cohen |
| 6,387,639 | B1 | 5/2002 | Posner et al. |
| 6,475,804 | B1 | 11/2002 | Lohse |
| 6,645,465 | B2 | 11/2003 | Hanash |
| 6,667,160 | B2 | 12/2003 | Fine |
| 7,205,117 | B1 | 4/2007 | Robertson et al. |
| 7,282,345 | B1 | 10/2007 | Hancock et al. |
| 7,402,403 | B1 | 7/2008 | Robertson et al. |
| 8,114,604 | B2 | 2/2012 | Robertson et al. |
| 2002/0168696 | A1 | 11/2002 | Hanash |
| 2003/0008332 | A1 | 1/2003 | Ryan et al. |
| 2003/0049692 | A1 | 3/2003 | Latov et al. |
| 2003/0099639 | A1 | 5/2003 | Rikihisa et al. |
| 2003/0138860 | A1 | 7/2003 | Robertson et al. |
| 2003/0232399 | A1 | 12/2003 | Robertson et al. |
| 2005/0084904 | A1 | 4/2005 | Laal et al. |
| 2005/0276485 | A1 | 12/2005 | Mori |
| 2006/0141547 | A1 | 6/2006 | Das et al. |
| 2007/0172487 | A1 | 7/2007 | Shih et al. |
| 2007/0224174 | A1 | 9/2007 | Kang et al. |
| 2008/0108084 | A1 | 5/2008 | Robertson et al. |
| 2008/0153113 | A1 | 6/2008 | Robertson et al. |
| 2008/0213921 | A1 | 9/2008 | Robertson et al. |
| 2009/0176319 | A1 | 7/2009 | Robertson et al. |
| 2012/0115749 | A1 | 5/2012 | Robertson et al. |
| 2013/0090251 | A1 | 4/2013 | Robertson et al. |

FOREIGN PATENT DOCUMENTS

| | | |
|---|---|---|
| EP | 236606 | 6/1992 |
| EP | 0684477 | 11/1995 |
| EP | 1200832 | 5/2006 |
| GB | 2395270 A | 5/2004 |

(Continued)

OTHER PUBLICATIONS

Kumar et al (Vet. Res., 2003, 34:71-83).*
Montenarh et al (International Journal of Oncology, 1998, 13: 605-610).*
Zhang et al (Cancer Epidemiol Biomarkers Prev, 2003, 12(2): 136-143).*
Pare et al (J Vet Diagn Invest, 1995, 7:352-359).*
Carlsson, et al., "Titration of Antibodies to Salmonella O Antigens by Enzyme-Linked Immunosorbent Assay", 1972, pp. 703-708, vol. 6, No. 5.
Dahlberg, et al., "Enzyme Linked Immunosorbent Assay for Titration of Haemophilus Influenzae Capsular and O Antigent Antibodies", Journal of Clinical Microbiology, 1980, pp. 185-192, vol. 12, No. 2.

(Continued)

*Primary Examiner* — Sean Aeder
(74) *Attorney, Agent, or Firm* — Kilpatrick Townsend & Stockton LLP

(57) ABSTRACT

The invention relates to a method of detecting a disease state or disease susceptibility in a mammalian subject which comprises detecting an antibody in a test sample comprising a bodily fluid from said mammalian subject wherein said antibody is a biological marker of a disease state or disease susceptibility, the method comprising: (a) contacting said test sample with a plurality of different amounts of an antigen specific for said antibody, (b) detecting the amount of specific binding between said antibody and said antigen, (c) plotting or calculating a curve of the amount of said specific binding versus the amount of antigen for each amount of antigen used in step (a) and (d) determining the presence or absence of said disease state or disease susceptibility based upon the amount of specific binding between said antibody and said antigen at each different antigen concentration used.

34 Claims, 12 Drawing Sheets

(56) References Cited

FOREIGN PATENT DOCUMENTS

| GB | 2426581 | 11/2006 |
|---|---|---|
| GB | 2426581 A | 11/2006 |
| GB | 2007/003486 | 12/2007 |
| GB | 2007/003486 SR | 12/2007 |
| JP | 7294530 | 11/1995 |
| JP | 9189702 | 7/1997 |
| JP | 11-230966 | 8/1999 |
| WO | WO-89/01153 | 2/1989 |
| WO | WO-92/13065 | 8/1992 |
| WO | WO-93/11236 | 6/1993 |
| WO | WO-93/21529 | 10/1993 |
| WO | WO-94/23728 | 10/1994 |
| WO | WO-96/00084 | 1/1996 |
| WO | WO-96/03502 A2 | 2/1996 |
| WO | 9711715 | 4/1997 |
| WO | WO-97/14794 | 4/1997 |
| WO | WO-98/55872 | 6/1998 |
| WO | WO-99/58978 A | 11/1999 |
| WO | WO-99/58978 A2 | 11/1999 |
| WO | WO-99/58979 | 11/1999 |
| WO | WO-00/26668 | 5/2000 |
| WO | WO 00/34787 | 6/2000 |
| WO | WO 0111372 | 2/2001 |
| WO | WO 02059617 | 8/2002 |
| WO | WO-2004/044590 | 5/2004 |
| WO | WO-2006/126008 A | 11/2006 |
| WO | WO-2008032084 | 3/2008 |

OTHER PUBLICATIONS

Giardina et al., Effect of Antigen Coating Conditions on Enzyme-Linked Immunosorbent Assay for Detection of Immunoglobulin G. Antibody to Neisseria Meningitidis Serogroup Y and W135 Capsular Polysaccharide Antigens in Serum, 2003, pp. 1136 - 1140, vol. 10, No. 6.

Munoz, et al., "New Experimental Criteria for Optimization of Solid-Phase Antigen Concentration and Stability in ELISA", 1986, pp. 137-144, vol. 94.

Rasmussen, et al., "An Elisa for the Detection of Anti-Neutrophil Cytoplasm Antibodies (ANCA)", Journal of Immunological Methods, 1990, pp. 139-145, vol. 127, No. 1.

Zielen, et al., "Simple Determination of Polysaccharide Specific Antibodies by Means of Chemically Modified ELISA Plates", 1996, pgs. 1-7, vol. 193, No. 1.

Definition of "monocyte" in On-line Medical Dictionary downloaded on Feb. 5, 2005 from url.www.cancerweb.ncl.ac.uk.

Aaronson, S. A. et al., "Characterization of Murine Sarcoma Virus (KIRSTEN) Transformation of Mouse and Human Cells", *J. Gen. Virol.* 1971, 13: 245-252; ATCC accession number CRL 1569, 245-252.

Agrawal, et al., "Cancer-associated MUC1 mucin inhibits human T-cell proliferation, which is reversible by IL-2", *Nature Medine* Jan. 1998, vol. 4, No.1, 43-49.

Ambrosini, G. et al., "A novel anti-apoptosis gene, survivin, expressed in cancer and lymphoma", *Nature Med* 1997, 3(8), 917-21.

Angelopoulou, K. et al., "Detection of the TP53 Tumour Suppressor Gene Product and p53 Auto-antibodies in the Ascites of Women with Ovarian Cancer", *European Journal of Cancer* Jan. 1997, Pergamon Press, Oxford, GB, vol. 33, No. 1, 115-121.

Anker, et al., "K-ras mutations are found in DNA extracted from the plasma of patients with colorectal cancer", *Gastroenterology* Apr. 1997, vol. 112, No. 4, 1114-1119.

Aparecida, et al., "Value of CEA Level Determination in Gallbladder Bile in the Diagnosis of Liver Metastases Secondary to Colorectal Adenocarcinoma", *Sao Paulo Medical Journal* 2001, vol. 119, No. 3, 110-113.

Apostolopoulos, et al., "MUC1 Cross-reactive Gala(1,3)GAL antibodies in humans switch immune responses from cellular to humoral", *Nature Medicine* 1998, vol. 4, 315-320.

Asano, et al., "Presence of anti-AFT-antibody producing B cells in peripheral blood lymphocyte of hepatocellular carcinoma patient", *Nippon Shokakibyo Gakkai Zasshi* Feb. 1984, 81(2):278.

Ayala, A. R. et al., "Human Chorionic Gonadotropin Immunoreactivity in Serum of Patients With Malignant Neoplasms", *Am J Reprod Immuno*. Apr-May 1983, 3(3), 149-51.

Baechstrom, et al., "Purification and Characterization of Sialyl-Le—Carrying Mucins of Human Bile; Evidence for the Presence of MUC1 and MUC3 Apoproteins", *The Journal of Biological Chemistry* 1994, vol. 269, No. 2, 14430-14437.

Barak, V. et al., "Clinical utility of cytokeratins as tumor markers", *Clin Biochem* Jul. 2004, 37(7), 529-40.

Barrette, Roger W. et al., "Quantifying Specific Antibody Concentrations by Enzyme-Linked Immunosorbent Assay Using Slope Correction", *Clinical and Vaccine Immunology* Jul. 2006, vol. 13, No. 7, 802-805.

Baselga, J. et al., "Phase II Study of Weekly Intravenous Recombinant Humanized Anti-p185 HER2 Monoclonal Antibody in Patients with HER2/neu-Overexpressing Metastatic Breast Cancer", *J. Clin Oncol*. 1996, 14(3), 737-744.

Batra, S. K. et al., "Expression of the Human MUC1 Mucin cDNA in a Hamster Pancreatic Tumor Cell Line HP-1", *Int. J. Pancreatology* 1992, 12:271-283.

Beatty, et al., "Biochemical Characterization of the Soluble Form of Tumor Antigen MUC1 Isolated from Sera and Ascites Fluid of Breast and Pancreatic Cancer Patients", Clinical Cancer Research 2001, vol. 7, 781-787.

Beatty, J. D. et al., "Measurement of monoclonal antibody affinity by noncompetitive enzyme immunoassay", *Journal of Immunological Methods* 1987, 100, 173-179.

Ben-Mahrez, et al., "Detection of circulating antibodies against c-myc protein in cancer patient sera", *British Journal of Cancer* 1988, 37:529-534.

Bhatti, et al., "Circulating Immunobiologic Markers in Prostatic Cancer and their Modulation by Surgical/Hormonal Therapy", *Journal of Tumor Marker Oncology* Summer-1994, vol. 9(2) 125-131.

Blackwood, Elizabeth M. et al., "Functional Analysis of the AUG- and CUG-Initiated Forms of the c-Myc Protein", *Molecular Biology of the Cell* 1994, 5: 597-609, 597-609.

Block, T. M. et al., "Use of targeted glycoproteomics to identify serum glycoproteins that correlate with liver cancer in woodchucks and humans", *Proc Natl Acad Sci USA* Jan. 18, 2005, 102(3), 779-84.

Booyse, F. M. et al., "Isolation and characterization of a urokinase-type plasminogen activator (MR = 54,000) from cultured human epithelial cells indistringuishable from urinary urokinase", J Biol Chem 1984, 259(11), 7198-205.

Braun, S. et al., "Cytokeratin-Positive Cells in the Bone Marrow and Survival of Patients with Stage I, II, or III Breast Cancer", *N. Engl J. Med* 2000, 342:8, 525-533.

Brichory, F. M. et al., "An Immune response manifested by the common occurrence of annexins I and II autoantibodies and high circulating levels of IL-6 in lung cancer", *Department of Pediatrics, Pathology and Surgery* 1998, 98(17), 9824-9829.

Butler, W. T. et al., "Osteopontin—Structure and biological activity", *CBA Foundation Symposia* 1988, 136, 203-206.

Callans, L. S. et al., "Raf-1 Protein Expression in Human Breast Cancer Cells", *Ann Surg Oncol* Jan 1995, 2(1):38-42.

Capella, G. et al., "Frequency and Spectrum of Mutations at Codons 12 and 13 of the C-K-ras Gene in Human Tumors", *Environ Health Perspectives* 1991, 93: 125-131.

Chari, S. et al., "Partial-Purification of Inhibin from Human Testicular Extracts", *ACTA Endocrinologia* 1977, 85 Suppl 212, 215-219.

Chen, Y. T. "A testicular antigen aberrantly expressed in human cancers detected by autologous antibody screening", *Proc. Nat. Acad. Sci* 1997, 94, 1914-1918.

Chinni, R. S. et al., "Humoral Immune Responses to Cathepsin D and Glucose-regulated Protein 78 in Ovarian Cancer Patients", *Clinical Cancer Research* Sep. 1997, 3, 1557-1564.

Clemmensen, I. et al., "Purification and characterization of a novel, oligomeric, plasminogen kringle 4 binding-protein from human plasma -tetranectin", *Eur J. Biochem* 1986, 156(2), 237-333.

Coussens, L. et al., "Tyrosine kinase receptor with extensive homology to EGF receptor shares chromosomal location with neu oncogene", *Science* 1985, 230, 1132-1139.

(56) References Cited

OTHER PUBLICATIONS

Croce, et al., "Expression of monoclonal-antibody-defined antigens in fractions isolated from human breast carcinomas and patient's serum", *Cancer. Immunol. Immunother*. 1995, vol. 40, 132-137.

Deguchi, et al., "Autoantibody to Human c-myc Oncogene Product in Autoimmune Patient's Sera", *Int. Arch. Allergy Appl. Immunol.* 1988, vol. 87, 313-316.

Denton, et al., "Induction of antibody responses to breast carcinoma associated mucins using synthetic peptide constructs as immunogens", *Cancer Letters* 1993, vol. 70, 143-150.

Devine, P. L. et al., "Circulating Mucins as Tumor Markers in Ovarian Cancer (Review)", *Anticancer Res.* May-Jun. 1992, 12(3), 709-17.

Diamandis, E. P. et al., "Human Tissue Kallikreins: A Family of New Cancer Biomarkers", Clin. Chem Aug. 2002, 48(8), 1198-1205.

Diamandis, E. et al., "Immunoassay", *Academic Press, San Diego, CA* 1996.

Diamandis, et al., "The new human kallikrein gene family: implications in carcinogenesis", *Trends Endocrinol Metab.* 11(2) Mar. 2000, 54-60.

Diamandis, E. P. et al., "The new human kallikrein gene family: implications in carcinogenesis", *Trends Endocrinol Metab* Mar. 2000, 11(2), 54-60.

Disis, et al., "High-Titer HER-2/neu Protein-Specific Antibody Can Be Detected in Patients With Early-Stage Breast Cancer", *Journal of Clinical Oncology* 1997, vol. 15, 3363-3367.

Downward, et al., "Close similarity of epidermal growth factor receptor and v-erb-B oncogene protein sequences", *Nature* 1984, 307, 521-527.

Dsouza, B. et al., "Collagen-induced morphogenesis and expression of the a2- integrin subunit is inhibited in c-erbB2-transfected human mammary epithelial cells", *Oncogene* 1993, 8, 1797/1806.

Duffy, M. J. "Carcinoembryonic antigen", *Clin. Chem* Apr. 2001, 47(4), 624-30.

Ellis, I. O. et al., "A monoclonal antibody, NCRC-11, raised to human breast carcinoma. 1. Production and immunohistological characterization", *Histopathology* 1984, 8: 501-516.

Fateh-Moghadam, et al., "Sensible use of tumour markers", *Verlag GMBH, ISBN* 3-926725-07-09 1993, Abstract only.

Fernandez-Madrid, F. "Autoantibodies to Annexin XI-A and Other Autoantigens in the Diagnosis of Breast Cancer", *Cancer Research* 2004, 64, 5089-5096.

Fishman, P. et al., "Application of autoantibodies to cancer therapy: A new concept", *The 9th International Congress of Immunology* 1995, 664.

Fossa, A. et al., "Identification of a nucleolar protein No55 as a tumour-associated auto-antigen in patients with prostate cancer", *Br J Cancer* 2000, 83(6), 743-9.

Gasperi-Campani, et al., "Chromosomal alterations, biological features and in vitro chemosensitivity of SCLC-R1, a new cell line from human metastatic small cell lung carcinoma", *European Journal of Cancer* Apr. 1998, vol. 34, No. 5, 724-730.

Gerke, V. "Annexins: From Structure to Function", *Physiological Reviews* 2002, 82, 331-371.

Gnudi, L. et al., "Adenovirus-Mediated Gene Transfer of Dominant Negative Rasasn17 in 3T3L 1 Adipocytes Does Not Alter Insulin-Stimulated P13-Kinase Activity of Glucose Transport", *Mol. Endocrinol.* 1997, 11, 67-76.

Gourevitch, et al., "Polymorphic epithelial mucin (MUC-1)-containing circulating immune complexes in carcinoma patients", *British Journal of Cancer* Oct. 1995, 72, 934-938.

Goydos, J. S. et al., "A Phase I Trial of a Synthetic Mucin Peptide Vaccine", *J. Surgical Res.* 1996, 63: 298-304.

Graham, R. A. et al., "The polymorphic epithelial mucin: potential as an immunogen for a cancer vaccine", *Cancer Immunol. Immunother* 1996, 42:71-80.

Green, et al., "Serum p53 Auto-antibodies: Incidence in Familial Breast Cancer", *European Journal of Cancer* 1994, vol. 30A, 580-584.

Gregory, JR, J. J. et al., "alpha-Fetoprotein and beta-Human Chorionic Gonadotropin. Their Clinical Significance as Tumour Markers", *Drugs* Apr. 1999, 57(4), 463-7.

Griffiths, B. et al., "Assignment of the polymorphic intestinal mucin gene MUC2 to chromosome-11p15", *Ann Hum Genet* 1990, 54:277-85.

Gure, "Human Lung Cancer Antigens Recognized by Autologous Antibodies: Definition of a Novel cDNA Derived from the Tumor Suppressor Gene Locus on Chromosome 3p21.3", *Ludwig Institute for Cancer Research* 1998, 1034-1040.

Haga, Y. et al., "Partial Purification and Characterization of CA19-9 Antigen from the Ascitic Fluid of a Patient with Pancreatic Cancer", *Clin Biochem* Oct. 22, 1989, (5)363-8.

Harlow, E. et al., "Antibodies: A Laboratory Manual", *Cold Spring Harbor Laboratory* 1988, 211-227.

Hayes, D. F. "Serum tumor markers for breast cancer", *Anticancer Drugs* Abstract 1995, vol. 6, suppl. 2, 26-27 (Abstract).

Hehir, Dermot J. et al., "C-myc Oncogene Expression: A Marker for Females at Risk of Breast Carcinoma", *Journal of Surgical Oncology* 1993, vol. 54, 207-210.

Hill, et al., "Nature of Carcinoembryonic Antigen Purified from Malignant Ascitic Fluid of Serous Cystadenocarcinoma of the Ovary", *Molecular Immunology* 1981, vol. 18, No. 7, 647-653.

Hinoda, et al., "Detection of a Circulating Antibody Against a Peptide Epitope on a Mucin Core Protein, MUC1, in Ulcerative Colitis", 1991, 163-168.

Houghton, et al., "Detection of Cell Surface and Intracellular Antigens by Human Monoclonal Antibodies—Hybrid Cell Lines Derived from Lymphocytes of Patients with Malignant Melanoma", *J. Exp. Med.* Jul. 1983, vol. 158, 53-65.

Hsu, W. M. et al., "GRP78 expression correlates with histologic differentiation and favorable prognosis in neuroblastic tumors", *Int J Cancer* Mar. 1, 2005, 113, 920-7.

Hudelist, G. et al., "Use of high-throughput protein array for profiling of differentially expressed proteins in normal and malignant breast tissue", *Breast Cancer Res treat.* Aug. 2004, vol. 86(3), 281-91.

Hudson, Gail A. et al., "Method for Testing Antiserum Titer and Avidity in Nephelometric Systems", *Clinical Chemistry* 1981, vol. 27, No. 11, 1838-1844.

Huhtala, M. L. et al., "Excretion of a tumor associated trypsin-inhibitor (TATI) in urine of patients with Gynecological Malignancy", *Int J Cancer* 1983, vol. 31(6), 711-714.

Ibrahim, S. O. et al., "Expression of biomarkers (p53, transforming growth factor alpha, epidermal growth factor receptor, c-erbB-2/neu and the proliferative cell nuclear antigen) in oropharyngeal squamous cell carcinomas", *Oral Oncology, Elsevier Science, Oxford, GB* May 1999, vol. 35, No. 3, 302-313.

Israeli, R. S. "Molecular Cloning of a Complementary DNA Encoding a Prostate-specific Membrane Antigen", *Cancer Res.* 1993, 53:227-30.

Jager, D. "Cancer-Testis Antigens and INGI Tumor Suppressor Gene Product Are Breast Cancer Antigens: Characterization of Tissue-specific INGI Transcripts and a Homologue Gene", *Cancer Res* Dec. 15, 1999, vol. 59(24), 6197-6204.

Jager, D. et al., "Identification of a tissue-specific putative transcription factor in breast tissue by serological screening of a breast cancer library", *Cancer Res* 2001, vol. 61(5), 2055-61.

Jais, et al., "Association of serum antibodies against p53 protein with poor survival in patients with Zolliger-Ellison Syndrome", *Gastroenterology* Jan. 1998, vol. 114, No. 1, 37-43.

Jalanko, et al., "Immunochemical properties of alpha-fetoprotein (AFP) and antibodies to autologous AFT", *Immunol. Commun* 1978, vol. 7, No. 2, 209-222.

Janeway, et al., "Competitive Inhibition Assay for Antigen in Unknown Samples",*Immunobiology* downloaded from url www.ncbi.nlm.nih.gov/books/bv.fcgi?rid=imm.figgrp.2140, total 2 pages 2001.

Jerome, K. R. et al., "A Survivor of Breast Cancer with Immunity to MUC-1 Mucin, and Lactational Mastitis", *Cancer Immunology and Immunotherapy* Jan. 1997, Berlin, DE, vol. 43, No. 6, 355-360.

Karanikas, et al., "Antibody and T Cell Responses of Patients with Adenocarcinoma Immunized with Mannan-MUC1 Fusion Protein", *J. Clin Invest.* 1997, vol. 100, No. 11, 2783-2792.

(56) References Cited

OTHER PUBLICATIONS

Karlan, B. Y. et al., "Peritoneal Serous Papillary Carcinoma, A Phenotypic Variant of Familial Ovarian Cancer: Implications for Ovarian Cancer Screening", *American Journal of Obstetrics & Gynecology* Apr. 1999, Mosby, St. Louis, MO, vol. 180, No. 4, 917-928.

Kasof, G. M. et al., "Livin, a novel inhibitor of apoptosis protein family", *J Biol Chem* 2000, vol. 276(5), 3238-46.

Kawahara, "Use of Four Monoclonal Antibodies to Detect Tumor Markers", *Cancer* 1986, vol. 58, 2008-2012.

Kiefer, M. C. et al., "The CDNA and derived amino-acid sequence for human Osteopontin", *Nucleic Acids Res* 1989, 17(8), 3306.

Kim, M. J. et al., "Clinicopathologic significance of the basal-like subtype of breast cancer: a comparison with hormone receptor and Her2/neu-overexpressing phenotypes",*Hum Pathol.*- Rpub Jul. 18, 2006 Sep. 2006, 37(9), 1217-26.

Kim, H. et al., "Human kallikrein gene 5 (KLK5) expression is an indicator of poor prognosis in ovarian cancer", *Br. J. Cancer* 2001, vol. 84(5), 643-650.

Kirchoff, C. "A major human epididymis-specific cDNA encodes a protein with sequence homology to extracellular proteinase-inhibitors", *Biology of Reproduction* 1991, 45(2), 350-357.

Kotera, et al., "Humoral Immunity against a Tandem Repeat Epitope of Human Mucin MUC-1 in Sera from Breast, Pancreatic, and Colon Cancer Patients", *Cancer Research* 1994, vol. 54, 2856-2860.

Krause, P. et al., "SeroGRID: an improved method for the rapid selection of antigens with disease related immunogenicity", *J Immunol Methods* Dec. 2003, vol. 283, 261-7.

Kumar, S. et al., "Standardisation and comparison of serial dilutions and single dilution enzyme linked immunosorbent assay (ELISA) using different antigenic preparations of the Babesia (Theileria) equi parasite", *Veterinary Research* 2003, vol. 34, No. 1 abstract, 71-83.

Kuralay, et al., "Diagnostic Usefulness of Tumour Marker Levels in Pleural Effusions of Malignant and Benign Origin", *Clinica Chimica Acta* 2000, vol. 300, 43-55.

Kutteh, W. H. et al., "Immunologic Characterization of Tumor Markers in Human Ovarian Cancer Cell Lines", *Journal of the Society for Gynecologic Investigation* 1996, vol. 3, No. 4, 216-222.

Laeng, et al., "Anti-Neural Autoantibodies, types 1 and 2: Their Utility in the Study of Tumors of the Nervous System", *Acta Neuropathol* 1998, 329-339.

Lafond, R. E. et al., "Autoantibodies to c-myc protein: elevated levels in patients with African Burkitt's lymphoma and norman Ghanians", *Autoimmunity* 1992, vol. 13, No. 3, 215-224.

Lai, et al., "Presence of Serum Anti-P53 Antibodies is Associated with Pleural Effusions and Poor Prognosis in Lung Cancer Patients", *Clinical Cancer Research* 1998, vol. 4, 3025-3030.

Lawniczak, et al., "The Search for Tumor-Associated Proteins in Pleural Effusions by Means of Moniclonal Antibodies and a Dot Blot Assay", *Lung* 1992, vol. 170, 65-74.

Lindner, P. et al., "Specific Detection of His-Tagged Proteins with Recombinant Anti-His Tag scFv-Phosphatase or scFv-Phage Fusions", *Bio Techniques* 1997, 22 (1), 140-149.

Lloyd, K. O. et al., "Isolation and Characterization of Ovarian Cancer Antigen CA 125 Using a New Monoclonal Antibody (VK-8) Identification As a Mucin-Type Molecule", *Int. J. Cancer* 1997, 71: 842-850.

Luo, et al., "Identification of Heat Shock Protein 90 and Other Proteins as Tumour Antigens by Serological Screening of an Ovarian Carcinoma Expression Library", *British Journal of Cancer* 2002, 339-343.

Maeda, A. et al., "Aberrant Expression of Photoreceptor-specific Calcium-binding Protein (Recoverin) in Cancer Cell Lines", *Cancer Res.*2000 Apr. 1, 2000, 60(7);1914-20.

Mashino, K. et al., "Expression of multiple cancer-testis antigen genes in gastrointestinal and breast carcinomas", *Br. J. Cancer* 2001, 85(5):713-720.

Matlashewski, G. et al., "Isolation and characterization of a human p53 cDNA clone: expression of the human p53 gene." *Embo J.* 1984, 3:3257-3262.

McIntyre, et al., "Oral contraceptive usage and the expression of CA 15-3 and C-erB-2 in the saliva of healthy women", *Oral Radiology and Endodontics* Dec. 1999, vol. 88, No. 6, 687-690.

Meichenin, M et al., "Tk, a new colon tumor-associated antigen resulting from altered O-glycosylation", *Cancer Res* Oct. 1, 2000, 60 (19), 5499-507.

Mercer, D. W. "Use of Multiple Markers to Enhance Clinical Utility", *Immunology Series* 1990, vol. 53, 39-54.

Microbix Biosystems Inc., "Antigen titration using the Microbix IgG ELISA", *Product Technical Bulletin*, URL://http://web.archive.org/web/2005 0526 2316 23/http://www/microbix.com/products/PDFs/TB-93-1Antigen TitraionousingtheMicrobixlgG+ELISA.pdf 2005.

Mineva, I. et al., "Differential expression of alphaB-crystallin and Hsp27-1 in anaplastic thyroid carcinomas because of tumor-specific alphaB-crystallin gene (CRYAB) silencing", *Cell Stress & Chaperones* Autumn 2005, 10(3):171-84.

Molina, et al., "Use of serial carcinoembryonic antigen and CA 15.3 assays in detecting relapses in breast cancer patients", *Breast Cancer Res Treat* 1995, 36:41-48.

Moll, R. et al., "The Catalog of Human Cytokeratins: Patterns of Expression in Normal Epithelia, Tumors and Cultured Cells", *Cell* Nov. 31, 1982, 31(1), 11-24.

Montenarh, et al., "P53 Autoantibodies in the Sera, Cyst and Ascitic Fluids of Patients with Ovarian Cancer", *International Journal of Oncology* 1998, vol. 13, 605-610.

Mudenda, et al., "The relationship between serum p53 autoantibodies and characteristics of human breast cancer", *CR J Cancer* 1994, 69:4445-4449.

Munemitsu, S. et al., "Regulation of intracellular B-catenin levels by the adenomatous polyposis coli (APC) tumor-suppressor protein", *PNAS* 1995, 92: 3046-50.

Munoz, et al., "New experimental criteria for optimization of solid-phase antigen concentration and stability in ELISA", *J. Immunol. Methods* 1986, 20:137-44.

Muraki, M. et al., "Serum CUFRA 21-1 in Lung Cancer", *Fourth Dept. of Internal Medicine* 1996, 1274-1277.

Narod, "Genetic epidemiology of prostate cancer", *BBA-Reviews on Cancer* Jan. 1999, vol. 1423, No. 2, F1-F13.

Nery, "Isolation and Partial Characterization of Macromolecular Urinary Aggregates Containing Carcinoembryonic Antigen-Like Activity", *Br. J. Cancer* 1974, vol. 29, No. 413.

Norum, L. F. et al., "Elevated CA 125 in Breast Cancer—A Sign of Advanced Disease", *Tumour Biol.* Jul.-Aug. 2001, 22(4), 223-8.

Nouwen, E. J. et al., "Occurrence of the mucinous differentiation antigen CA125 in genital tract and conductive airway epithelia of diverse mammalian species (rabbit, dog, monkey)", *Differentiation* 1990, 45:192-198.

Nustad, et al., "Epitopes on CA 125 from Cervical Mucus and Ascites Fluid and Characterization of Six New Antibodies", *Tumor Biol.* 2002, 303-314.

Obiezu, C. V. et al., "Human tissue kallikrein gene family: applications in cancer", *Cancer Lett.* Jun. 2005, 224(1), 1-22.

Pandha, et al., "Cellular and humoral responses to KRAS polynucleotide vaccines", *Cancer Gene Therapy* 1997, vol. 4, No. 5, 310.

Pare, J. et al., "An enzyme-linked immunosorbent assay (ELISA) for serological diagnosis of neospora sp. infection in cattle", *Journal of Veterinary Diagnostic Investigation* 1995, AAVLD, Columbia MO, vol. 7, 352-359.

Pavelic, Z. et al., "Evaluation of c-myc proto-oncogene in primary human breast carcinomas", *Anticancer Research* Jul.-Aug. 1991, 11(4):1421-1428.

Pedrero, J. M. G. et al., "Annexin A1 Down-Regulation in Head and Neck Cancer Is Associated with Epithelial Differentiation Status", *American Journal of Pathology* 2004, 164(1). 73-79.

Perey, L. "Elevated CA125 levels in patients with metastatic breast carcinoma", *Br J Cancer* Oct. 1990, 62(4), 668-670.

Petrakou, et al., "Preliminary Studies on the Binding of Human Autoantibodies to the MUC1 Antigen", *International Journal of Oncology* 1997, vol. 11, Suppl., 902.

Petrarca, C. et al., "Human Antibodies Against the Polymorphic Epithelial Mucin in Ovarian Cancer Patients Recognise a Novel

(56) References Cited

OTHER PUBLICATIONS

Sequence in the Tandem Repeat Region", *European Journal of Cancer* 1996, vol. 32A, No. 12, 2155-2163.
Pratt, M. A. et al., "Estrogen activates raf-1 kinase and induces expression of EGR-1 in MCF-7 breast cancer cells", *Mol Cell Biochem* Dec. 1998, 189(1-2), 119-25.
Prezas, P. "Overexpression of the human tissue kallikrein genes KLK4, 5, 6, and 7 increases the malignant phenotype of ovarian cancer cells", *Biol. Chem.* Jun. 2006, 387(6), 807-811.
Raghava, G. P. et al., "Method for determining the affinity of monoclonal antibody using non-competitive ELISA: A computer program", *Journal of Immunoassay* 1994, 15(2), 115-128.
Rao, et al., "Detection of Human Ovarian Tumor Associated Antigens by Autologous Antibodies Isolated from Ovarian Carcinoma Ascites Fluid", *Proceedings of the American Association of Cancer Research Annual Meeting* 1987, vol. 28 #1419, 358.
Rao, et al., "Detection of human ovarian tumor-associated antigens by antibodies isolated from ovarian carcinoma ascitic fluid", *Am J Obstet Gynecol* Jul. 1998, vol. 159, 94-98.
Reddish, M. A. et al., "Pre-immunotherapy serum CA27.29 (MUC-1) mucin level and CD69+lymphocytes correlate with effects of Theratope siayl-Tn-KLH cancer vaccine in active specific immunotherapy", *Cancer Immunol. Immunother* 1996, 42: 303-309.
Reiter, R. E. et al., "Prostate stem cell antigen: A cell surface marker overexpressed in prostate cancer", *Proc Nat. Acad. Sci.* 1998, 95:1735-1740.
Riddle, O. et al., "The preparation, identification and assey of prolactin—A hormone of the anterior pituitary", *Am J. Physiol* 1933, 105(1), 191-216.
Robertson, J.F.R. et al., "Assessment of Four Monoclonal Antibodies as Serum Markers in Breast Cancer", *Eur. J. Cancer* 1990, 26: 1127-1132.
Robertson, J.F. R. et al., "Prospective assessment of the role of five tumour markers in breast cancer", *Cancer Immunol. Immunother.* 1991, 33:403-410.
Robertson, et al., "Radioimmunohistochemistry of Epidermal Growth Factor Receptor in Breast Cancer", *Archives of Pathology and Laboratory Medicine* 2001, 126:177-81.
Rosenberg, R. S. et al., "Modulation of Androgen and Progesterone Receptors by Phytochemicals in Breast Cancer Cell Lines", *Biochem Biophys Res Commun.* 1998, 248:935-939.
Rughetti, et al., "Human B-Cell Immune Response to the Polymorphic Epithelial Mucin1", *Cancer Research* Jun. 1, 1993, 53, pp. 2457-2459.
Rusciano, "Conomitant Purification of Prostatic Carcinoma Tumor Markers from Human Seminal Fluid Under Nondenaturing Conditions", *Clinical Chemistry* 1988, vol. 34, No. 12, 2528-2532.
Sahin, et al., "Human neoplasms elicit multiple specific immune responses in the autologous host", *PNAS* 1995, vol. 92, 11810-11813.
Sandrin, "Natural human anti-Gala(1,3)Gal antibodies react with human mucin peptides", *Glycoconiugate Journal* 1997, 14:97-105.
Scanlan, et al., "Characterization of Human Colon Cancer Antigens Recognized by Autologous Antibodies", *International Journal of Cancer* 1998, vol. 76, 652-658.
Schneider, J. "P53 protein, EGF Receptor, and Anti-P53 Antibodies in Serum from Patients with Occupationally Derived Lung Cancer", *British Journal of Cancer* 1999, vol. 80, No. 12, 1987-1994.
Scully, R. et al., "BRCA1 is a component of the RNA polymerase II holoenzyme", *PNAS* 1997, 94: 5605-10.
Seabury, C. A. et al., "Evaluation of a new serum testing method for detection of prostate cancer", *J Urol* Jul. 2002, 168(1):93-9.
Seitz, S. et al., "Genetic Background of Different Cancer Cell Lines Influences the Gene Set Involved in Chromosome 8 Mediated Breast Tumor Suppression", *Genes Chromosomes Cancer* Jun. 2006, 45(6), 612-27.
Sharan, S. K. et al., "Embryonic lethality and radiation hypersensitivity mediated by Rad51 in mice lacking Brca2", *Nature* 1997, 386: 804-810.

Shibata, et al., "Purification and Characterizaton of Prostate Specific Antigen from Human Urine", *Biochimica et Biophysica Acta* 1997, vol. 1336, 425-433.
Sokoloff, et al., "A dual-Monoclonal Sandwich Assay for Prostate-Specific Membrane Antigen: Levels in Tissues, Seminal Fluid and Urine", *The Prostate* 2000, vol. 43, 150-157.
Soussi, T. "The humoral response to the tumor-suppressor gene-product p53 in human cancer: implications for diagnosis and therapy", *Immunology Today* Aug. 1996, Elsevier Publications, Cambridge GB, vol. 17, No. 8, 354-356.
Standker, L. et al., "Isolation and characterizaton of the circulating form of human endostatin", *FEBS Lett* 1997, 420 (2-3), 129-33.
Stearns, et al., *Breast Cancer Research and Treatment* Abstract Feb. 8, 1998, vol. 52, 239-259 (Abstract only).
Stedman, "Stedman's Medical Dictionary 27th Edition Definition of Fluid", http://www.thomsonhc.com/pdrel/librarian 2004, Definitions of several words accessed Dec. 17, 2007, 1-3.
Steiber, P. et al., "CYFRA 21-1, A New Marker in Lung Cancer", 1993, 707-713.
Stiller, D et al., "Immunohistochemical demonstration of alpha-fetoprotein in testicular germ cell tumors", *Acta Histochem Suppl.* 1986, Supp - Band 33:225-31.
Stockert, E. et al., "A Survey of the Humoral Immune Response of Cancer Patients to a Panel of Human Tumor Antigens", *Journal of Experimental Medicine* 1998, 187 (8), 1349-1354.
Strnad, N. et al., "Simple determination of polysaccharide specific antibodies by means of chemically modified ELISA plates", *Journal of Immunological Methods* Jun. 14, 1996, Elsevier Science Publishers B.V., vol. 193, No. 1, 1-7.
Stubbs, et al., "Faecal Carcinoembryonic Antigen (CEA) in Patients with Large Bowel Cancer", *European Journal of Surgical Oncology* 1987, vol. 13, 433-436.
Su, L. K. et al "Association between Wild Type and Mutant APC Gene Products", *Cancer Res.* 1993, 53:2728-2731.
Szala, S. et al., "Molecular cloning of cDNA for the carcinoma-associated antigen GA733-2", *Proc. Nat. Acad. Sci.* 1990, 87:3542-3546.
Tauchi, K. et al., "Expression of heat shock protein-70 and c-myc protein in human breast-cancer—an immunohistochemical study", *Jap J Clin Oncol* 1991, 21(4), 256-63.
Taylor-Papadimitriou, "Report on the First International Workshop on Carcinoma-Associated Mucins", *Int. J. Cancer* 1991, 49:1-5.
Thomas, W. M. et al., "Failure of CA19-9 to detect asymptomatic colorectal carcinoma", *Br. J. Cancer* 1991, 63:975-976.
Tondini, et al., "Comparison of CA15-3 and Carcinoembryonic Antigen in Monitoring the Clinical Course of Patients with Metastatic Breast Cancer", *Cancer Research* 1988, vol. 48, No. 14, 4107-4112.
Toth, et al., "A Carcinoembryonic Antigen (CEA) Binding Protein from Ascites Influnces CEA Uptake by Macrophages", *Biochemical and Biophysical Research Communications* 1990, vol. 171, No. 2, 633-640.
Tsai, et al., "Relationship of serum alpha-fetoprotein to circulating immune complexes and complements in patients with hepatitis B surface antigen-positive hepatocellular carcinoma", *Gastroenterol Jpn* Jun. 1990, 25(3), 338-93.
Tsujimoto, Y. et al., "Analysis of the structure, transcripts, and protein products of Bcl-2, the gene involved in human follicular lymphoma", *PNAS USA* 1986, 83(14), 5214-8.
Van Milligen, Florine J. et al., "Calculation of the affinity constant KASS for solid phase antigen: A model system using monoclonal antibodies against the cat allergen Fel d I", *Journal of Immunological Methods* 1993, 162:165-173.
Venegas, et al., "Purification and Immunochemical Characterization of Ascitic Fluid Glycoproteins Containing Certain Tumor-Associated and Blood Group Antigen Markers", *Glycoconjugate Journal* 1989, vol. 6, 551-524.
Voet, et al., *Biochemistry* 1990, 78, 1096, 1098.
Volkmann, M. et al., "Anti-p53 autoantibodies as serological marker in different tumor-entities", *Clinical Chemistry* Jul. 1995, vol. 41, No. S6 part 2, S221-S222.

(56) References Cited

OTHER PUBLICATIONS

Von Mensdorf-Pouilly, S. "Humoral Immune Response to Polymorphic Epithelial Mucin (MUC-1) inpatients with Benign and Malignant Breast Tumours", *European Journal of Cancer* 1996, vol. 32A, No. 8, 1325-1331.

Von Mensdorff-Pouilly, et al., "Circulating MUC1 Antibodies in Humans are Directed to More than One Region Within the MUC1 Mucin Peptide Core", *Anticancer Research* Nov. - Dec. 1997, vol. 17, 4184.

Warri, A. M. et al., "Anti-oestrogen Stimulation of ERBB2 Ectodomain Shedding from BT-474 Human Breast Cancer Cells with ERBB2 Gene Amplification", *Eur. J. Cancer* 1996, 32A: 134-140.

Wolf, A. et al., "A Tumour-Associated Antigen from the Pleural Effusion of Patients with Squamous-Cell Carcinoma of Lung", *Br. J. Cancer* 1978, vol. 36, 1046-1052.

Wolf, D. et al., "In Vitro Expression of Human p53 cDNA Clones and Characterization of the Cloned Human p53 Gene", *Mol. Cell. Biol.* 1985, 5(8):1887-1893.

Wu, Hy et al., "The expression of BIRC7 protein and mRNA in non-Hodgkin's lymphoma", *Leukemia & Lymphoma* 2006, 47(6), 1110-6.

Xing, P. X. et al., "Phase I study of synthetic MUC1 peptides in breast cancer", *Int. J.Oncol.* 1995, 6(6): 1283-1289.

Yamamoto, et al., "Detection of auto-antibodies against c-Myc in sera from lung cancer patients", *Proc. Amer. Soc. Cancer Res.* Abstract 1997, 564.

Yamamoto, et al., "L-Myc Overexpression and Detection of Auto-Antibodies Against L-Myc in both the Serum and Pleural Effusion from a Patient with Non-Small Cell Lung Cancer", *Internal Medicine* 1997, vol. 36, No. 10, 724-727.

Yamauchi, et al., "Autoantibodies to C-MYC Nuclear Protein Products in Autoimmune Disease", *Immunology* Jan. 1990, 69(1):117-20.

Yang, D-K et al., "Development and evaluation of indirect ELISA for the detection of antibodies against Japanese encephalistis virus in swine", *Journal of Veterinary Science* Sep. 30, 2006, vol. 7, No. 3, 271-275.

Yazici, H. et al., "Amplification in tumors and benign tissue of breast cancer patients", *Cancer Lett.* 1993, 107: 235-239.

Yousef, G. M. et al., "Expanded Human Tissue Kallikrein Family—A Novel Panel of Cancer Biomarkers", *Tumor Biol* 2002, 23, 185-192.

Zehentner, B. K. et al., "Mammaglobin as a Novel Breast Cancer Biomarker: Multigene Reverse Transcription-PCR Assay and Sandwich ELISA", *Clin Chem* Nov. 2004, 50(11), 2069-76.

Zehentner, B. K. et al., "Mammaglobin: a candidate diagnostic marker for breast cancer", *Clin Biochem.* Apr. 2004, 37(4), 249-57.

Zhang, J. et al., "Enhancement of Antibody Detection in Cancer Using Panel of Recombinant Tumor-associated Antigens", *Cancer Epidermiology, Biomarkers & Prevention* 2003, vol. 12, 136-143.

Zisman, et al., "Autoantibodies to Prostate Specific Antigen in Patients With Benign Prostatic Hypersplasia", *Journal of Urology* 1995, vol. 154, 1052-1055.

Szekanecz, et al., "Increased production of the soluble tumor-associated Antigens CA19-9, CA125, and CA15-3 in rheumatoid arthritis; potential adhesion molecules in synovial inflammation?", *ANN. NY Acad Sci* 2007, 1108:359-371.

Treon, et al., "Elevated soluble MUC1 levels and decreased anti-MUC1 antibody levels in patients with multiple myeloma", *Blood* 2000, (96)6, pp. 3147-3153.

GB0725239.8 Search Report dated Apr. 24, 2008.

PCT/GB2008/004260 International Search Report and Written Opinion, mailed Feb. 27, 2009

Chapman, C.J. et al., "Autoantibodies in lung cancer: possiblities for early detection and sbusequent cure", *Thorax* Sep. 26, 2007, 0:1-6. doi:10.1136/thx.2007.083592.

He, Ping et al., "Proteomics-based identification of alpha-enolase as a tumor antigen in non-small lung cancer", *Cancer Sci* Aug. 2007, 98(8), 1234-1240.

Lindner, et al., "Specific Detection of His-Tagged Proteins with Recombinant Anti-His Tag scFv-Phosphatase or scFv-Phage Fusions", *Biotechniques* 1997, vol. 22, 140-149.

Muraki, et al., "Assessment of serum CYFRA-21-1 in lung cancer", *Cancer* Apr. 1996, 77(7), 1274-7.

Schjetlein, Rune et al., "Choice of Standard Plasma for Diagnosis and Quantitation of Lupus Anticoagulants", *Thrombosis Research* 1993, 72:287-294.

Yamadori, et al., "A case of non-specific interstitial pneumonia associated with primary lung cancer: possible role of antibodies to lung cancer cells in the pathogenesis of non-specific interstitial pneumonia", *Respiratory Medicine* 1999, 93, 754-756.

"National Library of Medicine Gateway MeSH term definition downloaded from the Web", Apr. 23, 2009.

Canevari, et al., "1975-1995 Revised anti-cancer serological response: Biological significance and clinical implications", Annals of Oncology 1996, vol. 7, pp. 227-232.

Lubin, et al., "Analysis of p53 Antibodies in Patients with Various Cancers Define B-Cell Epitopes of Human p53: Distribution on Primary Structure and Exposure on Protein Surface", Cancer Research 1993, vol. 53, pp. 5872-5876.

Moingeon, "Strategies for designing vaccines eliciting Th1 responses in humans", Journal of Biotechnology 2002, vol. 98, pp. 189-198.

O'Sullivan, et al., "Polymorphic epithelial mucin from the sera of advanced breast cancer patients—isolation and partial characterisation", British Journal of Cancer 1990, vol. 61, pp. 801-808.

"Cell and Molecular Biology of Vertebrate Hard Tissues", Ciba Foundation Symposium 136.

Lederman, Seth et al., "A Single Amino Acid Substitution in a Common African Allele of the CD4 Molecule Ablates Binding of the Monoclonal Antibody, OKT4", Molecular Immunology 1991, vol. 28, No. 11, 1171-1181.

Li, Choh H. et al., "B-Endorphin omission analogs: Dissociation of immunoreactivity from other biological activities", Proc. Natl. Acad. Sci. Jun. 1980, vol. 77, No. 6, 3211-3214.

Notice of Allowance dated Jul. 9, 2013 in U.S. Appl. No. 10/534,773, 10 pages.

Final Office Action dated Jul. 3, 2013 in U.S. Appl. No. 11/681,830, 18 Pages.

Notice of Allowance dated May 30, 2013 in U.S. Appl. No. 11/854,050, 6 pages.

Final Office Action dated Jun. 5, 2013 in U.S. Appl. No. 12/343,047, 24 pages.

Non Final Office Action dated Sep. 19, 2013 in U.S. Appl. No. 13/349,348, 13 pages.

Hirasawa et al., "KL-6, a human MUC1 mucin, is chemotactic for human fibroblasts.", American Journal of Respiratory Cell and Molecular Biology [1997, 17(4):501-507].

Lenner et al., "Serume antibodies against p53 in relation to cancer risk and prognosis in breast cancer: a population-based epidemiological study", British Journal of Cancer, Feb. 1999, vol. 79, pp. 927-932.

Regidor et al., "Detection of p53 auto-antibodies in the aera of breast cancer patients with a new recurrence using an ELISA assay. Does a correlation with the recurrence free interval exist?", European Journal of Gynaecological Oncology, 1996, vol. 17, No. 3, pp. 192-199.

Sakurai et al., "Differential expression of the glycosylated forms of MUC1 during lung development", European Journal of Histochemistry 2007, vol. 51 issue 2 (Apr-Jun); 95-102.

Vennegoor et al., "Autoantibodies to p53 in ovarian cancer patients and healthy women: a comparison between whole p53 protein and 18-mer peptides for screening purposes", Cancer Letters, 1997, vol. 116, pp. 93-101.

U.S. Appl. No. 10/534,773, "Final Office Action", Feb. 22, 2013, 11 pages.

U.S. Appl. No. 11/681,830, "Non-Final Office Action", Dec. 5, 2012, 19 pages.

U.S. Appl. No. 12/343,047, "Office Action", Nov. 26, 2012, 19 pages.

U.S. Appl. No. 13/438,344, "Non-Final Office Action", Mar. 20, 2013, 7 pages.

Bellone et al., "Cancer immunotherapy: synthetic and natural peptides in the balance", Immunology Today, 1999, 20, pp. 457-462.

Ben-Efraim, "One Hundred Years of Cancer Immunotherapy: A Critical Appraisal", Tumor Biology, 1999, vol. 20(1), pp. 1-24.

(56) References Cited

OTHER PUBLICATIONS

Byers, "What can randomized controlled trials tell us about nutrition and cancer prevention?", CA Cancer Journal, vol. 49, No. 6, Nov./Dec. 1999, pp. 353-361.
Coomber et al., "Characterisation and clinicopathological correlates of serum anti-p53 antibodies in breast and colon cancer", J Cancer Res Clin Oncol, 1996, 122(12):757-62.
Frazer, "Is vaccine therapy the future in cancer prevention?", Expert Opinion on Pharmacotherapy, 2004, 5(12), pp. 2427-2434.
Granziero et al., "Adoptive immunotherapy prevents prostate cancer in a transgenic animal model", Eur J Immunol., Apr. 1999, vol. 29(4), pp. 1127-1138.
Graves et al., "Malignancy-induced autoimmunity to MUC1: initial antibody characterization", J. Peptide Res., 2005, 66: 357-363.
Harlow et al., "Antibodies: A Laboratory Manual", Cold Spring Harbor Laboratory, 1988, 562-563.
Hirasawa et al., "Natural Autoantibody to MUC1 is a Prognostic Indicator for Non-Small Cell Lung Cancer", Am J Respir Crit Care Med, 2000, 161:589-594.
Kohno et al., "Detection of Soluble Tumor-associated Antigens in Sera and Effusions Using Novel Monoclonal Antibodies, KL-3 and KL-6, against Lung Adenocarcinoma", Jpn. J. Clin. Oncol. 18: 203-216, 1988,.
Zhu et al., "Adenocarcinoma of Duodenum and Ampoulla of Vater: Clinicopathology Study and Expression of p53, c-neu, TGF-a, CEA, and EMA", Journal of Surgical Oncology, 1996, vol. 61; 100-105.

* cited by examiner

IMMUNOASSAY METHODS

CROSS REFERENCE TO RELATED APPLICATIONS

This application is the U.S. National Phase of PCT/GB2006/001944 filed on 26 May 2006 which claims the benefit of U.S. Provisional Patent Application No. 60/685,422 filed on 27 May 2005 and Great Britain Patent Application No. 0510943.4, filed 27 May 2005, the contents of which are incorporated by reference herein.

FIELD OF THE INVENTION

The invention generally relates to the field of diagnostic or prognostic assays and in particular relates to optimisation of assays for the detection of antibodies in a sample comprising patient bodily fluid, wherein such antibodies are used as biological markers of a disease state or disease susceptibility.

BACKGROUND TO THE INVENTION

Many diagnostic, prognostic and/or monitoring assays rely on detection of a biological marker of a particular disease state or disease susceptibility. Such biological markers are commonly proteins or polypeptides that are characteristic of a particular disease or associated with susceptibility to disease.

In recent years it has become apparent that antibodies, and in particular autoantibodies, can also serve as biological markers of disease or disease susceptibility. Autoantibodies are naturally occurring antibodies directed to an antigen which an individual's immune system recognises as foreign even though that antigen actually originated in the individual. They may be present in the circulation as circulating free autoantibodies or in the form of circulating immune complexes consisting of autoantibodies bound to their target marker protein. Differences between a wild type protein expressed by "normal" cells and an altered form of the protein produced by a diseased cell or during a disease process may, in some instances, lead to the altered protein being recognised by an individual's immune system as "non-self" and thus eliciting an immune response in that individual. This may be a humoral (i.e. B cell-mediated) immune response leading to the production of autoantibodies immunologically specific to the altered protein.

WO 99/58978 describes methods for use in the detection/diagnosis of cancer which are based on evaluating the immune response of an individual to two or more distinct tumour markers. These methods generally involve contacting a sample of bodily fluid taken from the individual with a panel of two or more distinct tumour marker antigens, each derived from a separate tumour marker protein, and detecting the formation of complexes of the tumour marker antigens bound to circulating autoantibodies immunologically specific for the tumour marker proteins. The presence of such circulating autoantibodies is taken as an indication of the presence of cancer.

Assays which measure the immune response of the individual to the presence of tumour marker protein in terms of autoantibody production provide an alternative to the direct measurement or detection of tumour marker protein in bodily fluids. Such assays essentially constitute indirect detection of the presence of tumour marker protein. Because of the nature of the immune response, it is likely that autoantibodies can be elicited by a very small amount of circulating tumour marker protein and indirect methods which rely on detecting the immune response to tumour markers will consequently be more sensitive than methods for the direct measurement of tumour markers in bodily fluids. Assay methods based on the detection of autoantibodies may therefore be of particular value early in the disease process and possibly also in relation to screening of asymptomatic patients, for example in screening to identify individuals "at risk" of developing disease amongst a population of asymptomatic individuals, to identify individuals who have developed a disease amongst a population of asymptomatic individuals. In addition the method based on the detection of autoantibodies may be of particular value early in the disease process and possibly also may be used to identify individuals who have developed a disease amongst a population of symptomatic individuals. Furthermore, they may be useful for earlier detection of recurrent disease. The assay methods may also be a value in selecting or monitoring therapies for a disease.

Antibodies and autoantibodies can also serve as biological markers of other disease states or disease susceptibilities, of which rheumatoid arthritis, systemic lupus erythematous (SLE), primary biliary cirrhosis (PBC), autoimmune thyroiditis (eg Hashimoto's thyroiditis), autoimmune gastritis (eg pernicious anaemia), autoimmune adrenalitis (eg Addison's disease), autoimmune hypoparathyroidism, autoimmune diabetes (eg Type 1 diabetes), myasthenia gravis are but examples.

The present inventors have recognised that when assays based on detection of antibodies are used diagnostically or prognostically to assess the disease state, disease progression or disease susceptibility of an individual within a population, difficulties can arise in devising a standardised assay methodology appropriate for the whole population of subjects to be screened because the absolute amounts of antibody present vary dramatically from individual to individual. This can produce a high incidence of false negative results, for example amongst individuals having a low amount of antibody. Similarly there is a difficulty in scoring true positive results because the variation in absolute amounts of antibody from individual to individual means that it is difficult to set a threshold for a positive assay result that is appropriate for all individuals within the population screened.

The present inventors have now determined that the performance and more specifically the clinical utility and reliability of assays based on detection of antibodies, particularly autoantibodies, as biological markers of disease can be improved dramatically by inclusion of an antigen titration step. By testing the sample suspected of containing antibodies against a series of different amounts of antigen and constructing a titration curve it is possible to reliably identify true positive screening results independently of the absolute amount of antibody present in the sample. Such an approach is contrary to prior art methods which titrate antigen merely to construct a calibration curve to allow identification of the most appropriate antigen concentration to be used for detecting antibodies in actual patient samples. In these methods only a single point measurement is proposed for actual diagnosis. Thus, these methods will not allow for variation in amounts of the antibody to be detected from individual to individual resulting in the incidence of false positives and false negatives as discussed. The present inventors have found that the antigen titration method of the invention discussed herein has greater specificity and sensitivity than measuring autoantibody reactivity at a single antigen concentration or methods in which the serum sample is titrated rather than the antigen.

SUMMARY OF THE INVENTION

According to a first aspect of the invention there is provided a method of detecting a disease state or disease susceptibility in a mammalian subject which comprises detecting an antibody in a test sample comprising a bodily fluid from said mammalian subject wherein said antibody is a biological marker of a disease state or disease susceptibility, the method comprising:
(a) contacting said test sample with a plurality of different amounts of an antigen specific for said antibody,
(b) detecting the amount of specific binding between said antibody and said antigen,
(c) plotting or calculating a curve of the amount of said specific binding versus the amount of antigen for each amount of antigen used in step (a) and
(d) determining the presence or absence of said disease state or disease susceptibility based upon the amount of specific binding between said antibody and said antigen at each different antigen concentration used.

According to a second aspect of the invention there is provided a method of detecting an antibody in a test sample comprising a bodily fluid from a mammalian subject, wherein said antibody is directed to a foreign substance introduced into said mammalian subject, the method comprising:
(a) contacting the test sample with a plurality of different amounts of an antigen specific for said antibody,
(b) detecting the amount of specific binding between said antibody and said antigen, and
(c) plotting or calculating a curve of the amount of said specific binding versus the amount of antigen for each amount of antigen used in step (a).

According to a third aspect of the invention there is provided a method of detecting an antibody in a test sample comprising a bodily fluid from a mammalian subject wherein said antibody is a biological marker of a disease state or disease susceptibility, the method comprising:
(a) contacting the test sample with a plurality of different amounts of an antigen specific for said antibody,
(b) detecting the amount of specific binding between said antibody and said antigen, and
(c) plotting or calculating a curve of the amount of said specific binding versus the amount of antigen for each amount of antigen used in step (a).

In all aspects of the invention the mammalian subject is preferably a human.

In all aspects of the invention the method is preferably carried out in vitro on a test sample comprising a bodily fluid obtained or prepared from the mammalian subject.

A particular feature of the invention in all its aspects is that the judgement as to whether the relevant antibody is or is not present in the test sample is based upon the amount of specific binding observed at each different antigen concentration tested, in other words the collective values, rather than just a reading at a single concentration. Thus, the determination of the presence or absence of disease state or disease susceptibility or antibodies to a foreign substance in a patient sample can follow based directly on these collective values. Preferably, the judgement is made on the basis of the showing of a generally S-shaped or sigmoidal curve when the amount of specific binding is plotted against the amount of antigen. As will be apparent from the Examples herein the inventors have observed that the antigen titration methods of the invention have higher specificity and sensitivity than methods of diagnosis or detection based upon a single reading and reduce incidence of false positive and false negative determinations.

DETAILED DESCRIPTION OF THE INVENTION

Figure 1:
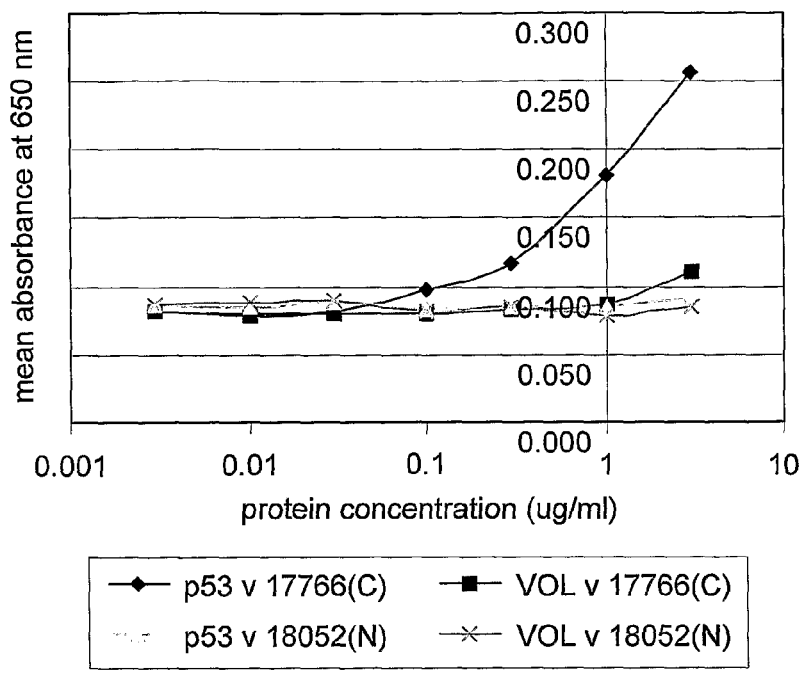
FIG. 1: Measurement of autoantibodies in serum using an antigen titration curve. Cancer patient serum 17766(C) binds strongly to the test antigen with a characteristic sigmoidal curve ( (—◆—) ) but does not bind to the negative control, VOL ( (—■—) ). In comparison, serum from a normal individual, 18052(N) does not bind to the test antigen ( (—▲—) ) or to the negative control ( (—✕—) ).

The invention in general provides an immunoassay method for detecting an antibody which serves as a biological marker for a disease state or disease susceptibility, characterised in that a sample to be tested for the presence of the antibody is tested for specific binding against different amounts of antigen specific for the antibody and a titration curve produced for antibody/antigen binding versus the amount of antigen tested.

The general features of immunoassays, for example ELISA, radioimmunoassays and the like, are well known to those skilled in the art (see Immunoassay, E. Diamandis and T. Christopoulus, Academic Press, Inc., San Diego, Calif., 1996). Immunoassays for the detection of antibodies having a particular immunological specificity generally require the use of a reagent (antigen) that exhibits specific immunological reactivity with the antibody under test. Depending on the format of the assay this antigen may be immobilised on a solid support. A sample to be tested for the presence of the antibody is brought into contact with the antigen and if antibodies of the required immunological specificity are present in the sample they will immunologically react with the antigen to form antibody-antigen complexes which may then be detected or quantitatively measured.

The method of the invention is characterised in that a standardised sample to be tested for the presence of the antibody is tested against a plurality of different amounts of antigen (also referred to herein as a titration series). The sample is tested against at least two, and preferably at least three, four, five, six or seven different amounts of the antigen. Typical assays may also include a negative control which does not contain any antigen.

In this context the term "antigen" refers to a substance comprising at least one antigenic determinant or epitope capable of interacting specifically with the target antibody it is desired to detect or any capture agent interacting specifically with the variable region or complementary determining regions of said antibody. The antigen will typically be a naturally occurring or synthetic biological macromolecule such as for example a protein or peptide, a polysaccharide or a nucleic acid and can include antibodies or fragments thereof such as anti-idiotype antibodies.

Skilled readers will appreciate that in the method of the invention the amount of antigenic determinants or epitopes available for binding to the target antibody is important for establishing a titration series. In many assay formats the amount of antigenic determinants or epitopes available for binding is directly correlated with the amount of antigen molecules present. However, in other embodiments, such as certain solid phase assay systems, the amount of exposed antigenic determinants or epitopes may not correlate directly with the amount of antigen but may depend on other factors, such as attachment to the solid surface. In these embodiments, references herein to "different amounts of antigen" in a titration series may be taken to refer to different amounts of the antigenic determinant or epitope.

The relative or absolute amount of specific binding between antibody and antigen is determined for each different amount of antigen (antigenic determinant or epitope) used and used to plot or calculate a curve of the (relative or absolute) amount of specific binding versus the amount of antigen for each amount of antigen tested. Typical results are illustrated, by way of example only, in the accompanying Figures for detection of a number of different antibodies. The presence in the test sample of antibody reactive with the antigen used in the assay is determined based upon the amount of specific binding observed at each antigen amount and is generally indicated by a generally S-shaped or sigmoidal curve. The absolute amounts of specific binding between antibody and antigen are generally not material, unless it is desired to produce a quantitative measurement. For a simple yes/no determination of the presence or absence of antibodies it is sufficient only that a curve of the correct shape is produced. If there is no variation in detectable binding over the different amounts of antigen tested then this can be scored as an absence of a detectable amount of the antibody. In preferred embodiments of the invention the method is non-quantitative. It can thus give a yes/no determination of presence or absence of antibody using a dimensionless proportional relationship which is independent of signal strength.

A measure of the amount of antibody present in a particular sample can, if desired, be derived from the results of antigen titration assays.

The method of the invention is advantageous for use in clinical diagnostic, prognostic, predictive and/or monitoring assays where the absolute amounts of target antibody present can vary enormously from patient-to-patient. The inventors have observed that if such assays are based on detection of antibody binding using a single amount/concentration of test antigen, patient samples containing an amount of antibody which is at the very low or the very high end of the normal physiological range of amount of antibody across the population can be missed due to limitations of the assay methodology; samples with a low amount of antibody may be scored as false negative results, whereas those with very high levels of antibody may be off the scale for accurate detection within the chosen assay methodology.

The titration assay method of the invention is also particularly suitable for the detection of antibodies/autoantibodies as biological markers of disease state or susceptibility where there is considerable patient-to-patient variation in the specificity and affinity of the antibodies/autoantibodies for target antigen. Autoantibody responses by their very nature can vary significantly from patient-to-patient, with variation occurring both in the absolute amounts of autoantibody present and in the specificity/affinity of the autoantibodies. The method of the invention can take account of this patient-to-patient variation, thus enabling a standard assay format to be developed for any given antibody/autoantibody.

Interactions between autoantibodies and their target antigens are generally of low affinity but the strength of binding may vary from patient-to-patient, as outlined above. The method of the invention is particularly suited to detection of low affinity binding, as a positive result can be inferred from the shape of the titration curve.

The method of the invention also provides a safeguard against day-to-day variation in the performance of immunoassays used for detection of autoantibodies/antibodies for diagnostic, prognostic and/or monitoring (disease state or therapy) purposes. It is often observed that there can be considerable day-to-day variation in signal strength when carrying out immunoassays for detection of antibodies in samples comprising patient bodily fluids. Such variation might arise, for example, because of differences in the way in which the samples were obtained and stored prior to testing. Such factors make it difficult to score the results of clinical assays with certainty, for example on the basis of a simple threshold value of antibody/antigen binding. The present invention minimises the effects of such day-to-day variation since a positive result for the presence of antibody is clearly evident from the shape of the titration curve, independent of signal strength.

Still further advantages of the method of the invention are that it allows dilution of the patient sample, yet still produces consistent results, and also that it will generally produce the same qualitative screening result (positive/negative) using bodily fluids from different sources in one individual (e.g. blood or serum versus ascites fluid or pleural effusion), even though the absolute concentration of antibodies may be different in the different fluids.

The method of the invention may be carried out in any suitable format which enables contact between a sample suspected of containing the antibody and multiple different amounts of an antigen. Conveniently, contact between the sample and different amounts of the antigen may take place in separate but parallel reaction chambers such as the wells of a microtitre plate. Varying amounts of the antigen can be coated onto the wells of the microtitre plate by preparing serial dilutions from a stock of antigen across the wells of the microtitre plate. The stock of antigen may be of known or unknown concentration. Aliquots of the test sample may then be added to the wells of the plate, with the volume and dilution of the test sample kept constant in each well. The absolute amounts of antigen added to the wells of the microtitre plate may vary depending on such factors as the nature of the target antibody, the nature of the sample under test, dilution of the test sample, etc, as will be appreciated by those skilled in the art. Generally the amounts of antigen and the dilution of the test sample will be selected so as to produce a range of signal strength which falls within the acceptable detection range of the read-out chosen for detection of antibody/antigen binding in the method. Typical amounts and dilutions for testing of human serum samples suspected of containing anti-tumour marker autoantibodies are given in the accompanying examples. Conveniently the tested amounts of antigen may vary in the range of from 0.01 µg/ml to 10 µg/ml.

As aforesaid, it is also possible to construct a titration curve starting with a single stock of antigen even when the absolute concentration of antigen in the stock is unknown. Provided that a same single stock solution is used and serially diluted in the same manner, it is possible to compare the results of separate titration assays for this antigen run on different starting test samples.

In a further embodiment different amounts of the antigen (antigenic determinants or epitopes) may be immobilised at discrete locations or reaction sites on a solid support. The entire support may then be brought into contact with the test sample and binding of antibody to antigen detected or measured separately at each of the discrete locations or reaction sites. Suitable solid supports also include microarrays, for example arrays wherein discrete sites or spots on the array comprise different amounts of the antigen. Microarrays can be prepared by immobilising different amounts of a particular antigen at discrete, resolvable reaction sites on the array. In other embodiments the actual amount of immobilised antigen molecules may be kept substantially constant but the size of the sites or spots on the array varied in order to alter the amount of binding epitope available providing a titration series of sites or spots with different amounts of available binding epitope. In such embodiments the two-dimensional surface concentration of the binding epitope(s) on the antigen is important in preparing the titration series, rather then the absolute amount of antigen. Techniques for the preparation and interrogation of protein/peptide microarrays are generally known in the art.

It will be understood from the above discussion that in all of the embodiments of the invention variation in the amount of antigen may be achieved by changing the antigen or epitope density against which the sample is tested, or by maintaining antigen or epitope density but increasing the surface area over which antigen is immobilized, or both.

Microarrays may be used to perform multiple assays for antibodies of different specificity on a single sample in parallel. This can be done using arrays comprising multiple sets of different antigens, each set comprising a particular antigen at multiple different amounts or concentrations. The term "different antigens" encompasses antigens derived from different proteins or polypeptides (such as antigens derived from unrelated proteins encoded by different genes) and also antigens which are derived from different peptide epitopes of a single protein or polypeptide. A given microarray may include exclusively sets of different antigens derived from different proteins or polypeptides, or exclusively sets of different antigens derived from different peptide epitopes of a single protein or polypeptide, or a mixture of the two in any proportion. It should be noted that each individual antigen set of different amounts or concentrations in any embodiment of the invention will generally comprise just one antigen and not mixtures thereof.

As used herein the term "bodily fluid", when referring to the material to be tested for the presence of antibodies using the method of the invention, includes inter alia plasma, serum, whole blood, urine, sweat, lymph, faeces, cerebrospinal fluid, ascites, pleural effusion, seminal fluid, sputum, nipple aspirate, post-operative seroma or wound drainage fluid. As aforesaid, the methods of the invention are preferably carried out in vitro on a test sample comprising bodily fluid removed from the test subject. The type of bodily fluid used may vary depending upon the identity of the antibody to be tested and the clinical situation in which the assay is used. In general, it is preferred to perform the assays on samples of serum or plasma. The test sample may include further components in addition to the bodily fluid, such as for example diluents, preservatives, stabilising agents, buffers etc.

The term "antigen" is used herein in a broad sense to refer to any substance which exhibits specific immunological reactivity with a target antibody to be detected. Suitable antigens may include, but are not limited to, naturally occurring proteins, recombinant or synthetic proteins or polypeptides, synthetic peptides, peptide mimetics, etc, also polysaccharides and nucleic acids. Specifically, where "antigen" is used herein it is intended to encompass any capture agent, whether of human origin, mammalian origin or otherwise, capable of specific immunological interaction with the variable or complementary determining regions of the antibody to be detected. For example anti-idiotypic antibodies may be regarded as an antigen for this purpose as may antigens generated by phage display.

Certain antigens may comprise or be derived from proteins or polypeptides isolated from natural sources, including but not limited to proteins or polypeptides isolated from patient tissues or bodily fluids. In such embodiments the antigen may comprise substantially all of the naturally occurring protein, i.e. protein substantially in the form in which it is isolated from the natural source, or it may comprise a fragment of the naturally occurring protein. To be effective as an antigen in the method of the invention any such "fragment" must retain immunological reactivity with the antibodies for which it will be used to test. Suitable fragments might, for example, be prepared by chemical or enzymatic cleavage of the isolated protein.

Depending on the precise nature of the assay in which it will be used, the antigen may comprise a naturally occurring protein, or fragment thereof, linked to one or more further molecules which impart some desirable characteristic not naturally present in the protein. For example, the protein or fragment may be conjugated to a revealing label, such as for example a fluorescent label, coloured label, luminescent label, radiolabel or heavy metal such as colloidal gold. In other embodiments the protein or fragment may be expressed as a fusion protein. By way of example, fusion proteins may include a tag peptide at the N- or C-terminus to assist in purification of the recombinantly expressed antigen.

Depending on the format of the assay in which it is to be used the antigen may be immobilised on a solid support such as, for example, the wells of a microtitre plate, microarray beads or chips or magnetic beads. Immobilization may be effected via non-covalent adsorption or covalent attachment. Any suitable attachment means may be used provided this does not adversely affect the ability of the antigen to immunologically react with the target antibody to a significant extent.

The invention is not limited to solid phase assays, but also encompasses assays which, in whole or in part, are carried out in liquid phase, for example solution phase bead assays.

In one embodiment, antigens may be labelled with a ligand that would facilitate immobilisation, such as biotin. The antigen can then be diluted to a suitable titration range and then allowed to react with autoantibodies in patient samples in solution. The resulting immune complexes can then be immobilised on to a solid support via a ligand-receptor interaction (e.g. biotin-streptavidin) and the remainder of the assay performed as described below.

To facilitate the production of biotinylated antigens for use in the assay methods of the invention, cDNAs encoding a full length antigen, a truncated version thereof or an antigenic fragment thereof may be expressed as a fusion protein labelled with a protein or polypeptide tag to which the biotin co-factor may be attached via an enzymatic reaction. Vectors for the production of recombinant biotinylated antigens are commercially available from a number of sources.

As illustrated in the accompanying examples, an additional advantage of the use of the titration curve approach with biotinylated antigens is that the assay is able to distinguish between binding of the biotin component to anti-biotin antibodies and true binding of the antigen to its cognate antibody. The inventors have observed that a significant number of the human population naturally produce anti-biotin antibodies which might lead to the production of false positive results in assays based on the use of biotinylated antigen.

As aforesaid, the "immunoassay" used to detect antibodies according to the invention may be based on standard techniques known in the art, with the exception that multiple amounts of antigen are used to create a titration curve. In a most preferred embodiment the immunoassay may be an ELISA. ELISAs are generally well known in the art. In a typical "indirect" ELISA an antigen having specificity for the antibodies under test is immobilised on a solid surface (e.g. the wells of a standard microtiter assay plate, or the surface of a microbead or a microarray) and a sample comprising bodily fluid to be tested for the presence of antibodies is brought into contact with the immobilised antigen. Any antibodies of the desired specificity present in the sample will bind to the immobilised antigen. The bound antibody/antigen complexes may then be detected using any suitable method. In one preferred embodiment a labelled secondary anti-human immunoglobulin antibody, which specifically recognises an epitope common to one or more classes of human immunoglobulins, is used to detect the antibody/antigen complexes. Typically the secondary antibody will be anti-IgG or anti-IgM. The secondary antibody is usually labelled with a detectable marker, typically an enzyme marker such as, for example, peroxidase or alkaline phosphatase, allowing quantitative detection by the addition of a substrate for the enzyme which generates a detectable product, for example a coloured, chemiluminescent or fluorescent product. Other types of detectable labels known in the art may be used with equivalent effect.

The invention relates to a method of detecting antibodies that are biological markers of a disease state or disease susceptibility. This particular aspect of the invention preferably excludes assays designed to test for antibodies produced as a result of a vaccine challenge or immunisation protocol, other than vaccination with cancer markers. Therefore, assays according to this aspect of the invention preferably do not include assays designed to test for the presence of anti-viral or anti-bacterial antibodies following vaccination/immunisation.

In certain embodiments of the invention the antibody may be an autoantibody. As indicated above, the term "autoantibody" refers to a naturally occurring antibody directed to an antigen which an individual's immune system recognises as foreign even though that antigen actually originated in the individual. Autoantibodies include antibodies directed against altered forms of naturally occurring proteins produced by a diseased cell or during a disease process. The altered form of the protein originates in the individual but may be viewed by the individual's immune system as "non-self" and thus elicit an immune response in that individual in the form of autoantibodies immunologically specific to the altered protein. Such altered forms of a protein can include, for example, mutants having altered amino acid sequence, optionally accompanied by changes in secondary, tertiary or quaternary structure, truncated forms, splice variants, altered glycoforms etc. In other embodiments the autoantibody may be directed to a protein which is overexpressed in a disease state, for as a result of gene amplification or abnormal transcriptional regulation. Overexpression of a protein which is not normally encountered by cells of the immune system in significant amounts can trigger an immune response leading to autoantibody production. In still further embodiments the autoantibody may be directed to a fetal form of a protein which becomes expressed in a disease state. If a fetal protein which is normally expressed only in early stages of development before the immune system is functional becomes expressed in a disease state, the fetal form may be recognised by the immune system as "foreign", triggering an immune response leading to autoantibody production.

In one embodiment the antibody may be an autoantibody specific for a tumour marker protein, and more particularly a "cancer-associated" anti-tumour autoantibody.

The term "cancer-associated" anti-tumour autoantibody refers to an autoantibody which is directed against an epitope present on forms of tumour marker proteins which are preferentially expressed in the cancer disease state. The presence of such autoantibodies is characteristic of the cancer disease state, or of pre-disposition to cancer in asymptomatic patients.

In preferred applications the method of the invention will be used to detect the presence of cancer-associated anti-tumour autoantibodies in human subjects or patients, and will most preferably take the form of an in vitro immunoassay, performed on a test sample comprising a sample of bodily fluid taken from the subject/patient. The sample of bodily fluid may be diluted in a suitable buffer or may be treated for long term storage or otherwise prior to testing.

In vitro immunoassays are non-invasive and can be repeated as often as is thought necessary to build up a profile of autoantibody production in a patient, either prior to the onset of disease, as in the screening of "at risk" individuals, or throughout the course of disease (further discussed below in relation to preferred applications of the method).

In particular, but non-limiting, embodiments the methods of the invention may comprise immunoassays to (simultaneously) detect two or more types of autoantibodies, each having specificity for different epitopes on the same or related tumour marker proteins (e.g. different isoforms or variants encoded by a single gene) or for epitopes on different tumour marker proteins (meaning proteins encoded by different genes). These methods will typically involve use of a panel of two or more sets of antigens, each set of antigens usually being derived from a different tumour marker protein (different in this context meaning proteins that are the products of different genes) although as noted above a set of antigens could also involve different epitopes on the same tumour marker protein. A set of antigens refers to single antigen to be tested at different amounts/concentrations in the method of the invention. These methods, which may be hereinafter referred to as "panel-assays", utilise a panel of two or more sets of antigens to monitor the overall immune response of an individual to a tumour or other carcinogenic/neoplastic change. These methods thus detect a "profile" of the immune response in a given individual, indicating which tumour markers elicit an immune response resulting in autoantibody production. The use of a panel of two or more antigens to monitor production of autoantibodies against two or more different tumour markers is generally more sensitive than the detection of autoantibodies to single markers and gives a much lower frequency of false negative results (see WO 99/58978 and WO 2004/044590, the contents of which are incorporated herein in their entirety by reference).

Therefore, in a non-limiting embodiment the invention provides a method of detecting two or more antibodies in a test sample comprising a bodily fluid from a mammalian subject wherein at least one of said antibodies is a biological marker of a disease state or disease susceptibility, the method comprising:
(a) contacting the test sample with two or more sets of antigens, wherein each one of said sets of antigens is specific for one of said antibodies to be detected in the test sample and wherein each set of antigens comprises a plurality of different amounts of said antigen,
(b) detecting the amount of specific binding between said antibodies and said antigens, and
(c) plotting or calculating a curve of the amount of said specific binding versus the amount of antigen for each set of antigens used in step (a).

In one embodiment each of said two or more antibodies will be a biological marker of a disease state or disease susceptibility, however it is within the scope of the invention to combine a titration assay for a disease marker antigen with a titration assay for any other type of antibody, which may or may not be a disease marker, in the same test sample.

Either way the judgement as to whether the relevant antibodies are or are not present in the test sample is based upon the amount of specific binding observed at each of the different antigen concentrations in respect of each different antigen in the test, in other words the collective values for each antigen rather than a reading at a single concentration for each antigen. Thus, the determination of presence or absence of disease state or disease susceptibility or antibodies to a foreign substance in a patient sample based upon presence of two or more types of antibody can be based on these collective values for each antigen. Preferably, the judgement is made on the basis of the showing of a generally S-shaped or sigmoidal curve in respect of any or all of the antigens present in the test.

For the avoidance of doubt, assays based on the use of a single type of antigen to detect antibodies may be referred to herein as "single marker assays", whereas assays based on the use of a panel of two or more antigens are referred to as "panel assays".

The method of the invention may be adapted for use in the detection of autoantibodies to essentially any tumour marker protein for which a suitable antigen may be prepared, as a single marker assay or as a component of a panel assay. In particular, the method may be adapted to detect/measure autoantibodies to the epidermal growth factor receptor protein EGFR (Downward et al (1984) Nature. 307: 521-527; Robertson et al. (2001 Archives of Pathology and Laboratory Medicine 126; 177-81), the glycoprotein MUC1 (Batra, S. K. et al. (1992) *Int. J. Pancreatology.* 12: 271-283) and the signal transduction/cell cycle regulatory proteins Myc (Blackwood, E. M. et al. (1994) *Molecular Biology of the Cell* 5: 597-609), p53 (Matlashewski, G. et al. (1984) *EMBO J.* 3: 3257-3262; Wolf, D. et al. (1985)*Mol. Cell. Biol.* 5: 1887-1893) and ras (or Ras) (Capella, G. et al. (1991) Environ Health *Perspectives.* 93: 125-131), and also BRCA1 (Scully, R. et al. (1997) *PNAS* 94: 5605-10), BRCA2 (Sharan, S. K. et al. (1997) *Nature.* 386: 804-810), APC (Su, L. K. et al. (1993)*Cancer Res.* 53: 2728-2731; Munemitsu, S. et al. (1995) *PNAS* 92: 3046-50), CA125 (Nouwen, E. J. et al. (1990) *Differentiation.* 45: 192-8), PSA (Rosenberg, R. S. et al. (1998) *Biochem Biophys Res Commun.* 248: 935-939), carcinoembryonic antigen CEA (Duffy, M. J. (2001)*Clin Chem*, April 47(4): 624-30), CA19.9 (Haga, Y. et al (1989)*Clin Biochem* (1989) October 22(5): 363-8), NY-ESO-1 (cancer/testis antigen; Chen, Y.-T. et al., Proc. Nat. Acad. Sci. 94: 1914-1918, 1997), PSMA (prostate specific membrane antigen; Israeli, R. S. et al., Cancer Res. 53: 227-230, 1993), PSCA (prostate stem cell antigen; Reiter, R. E. et al., Proc. Nat. Acad. Sci. 95: 1735-1740, 1998) and EpCam (epithelial cellular adhesion molecule; Szala, S. et al., Proc. Nat. Acad. Sci. 87: 3542-3546, 1990), HER2 (also known as c-erbB2 Coussens, L. et al., Science 230: 1132-1139, 1985), CAGE (Jager D, et al., Cancer Res. 1999 Dec. 15; 59(24):6197-204; Mashino K, et al., Br J. Cancer. 2001 Sep. 1; 85(5):713-20), cytokeratins (Moll R, et al., Cell. 1982 November; 31(1):11-24; Braun S, et al., N Engl J Med. 2000; 342: 525-533), recoverin (Maeda A, et al., Cancer Res. 2000 Apr. 1; 60(7):1914-20, kallikreins (Kim H, et al., Br J Cancer 2001; 84:643-650; Yousef G M, et al., Tumor Biol 2002; 23:185-192); annexins (Hudelist G, et al., Breast Cancer Res Treat. 2004 August; 86(3):281-91), α-fetoprotein (Stiller D, et al., Acta Histochem Suppl. 1986; 33:225-31), GRP78 (Block T M, et al., Proc Natl Acad Sci USA. 2005 Jan. 18; 102(3):779-84; Hsu W M, et al., Int J Cancer. 2005 Mar. 1; 113(6):920-7), CA125 (Norum L F, et al., Tumour Biol. 2001 July-August; 22(4):223-8; Perey L, et al., Br J Cancer. 1990 October; 62(4):668-70; Devine P L, et al., Anticancer Res. 1992 May-June; 12(3):709-17); mammoglobin (Zehentner B K, et al., Clin Chem. 2004 November; 50(11):2069-76; Zehentner B K, Carter D. Clin Biochem. 2004 April; 37(4):249-57), raf (Callans L S. et al., Ann Surg Oncol. 1995 January; 2(1):38-42; Pratt M A, et al., Mol Cell Biochem. 1998 December; 189(1-2):119-25), beta-human chorionic gonadotropin b-HCG (Ayala A R, et al., Am J Reprod Immunol. 1983 April-May; 3(3):149-51; Gregory J J Jr, et al., Drugs. 1999 April; 57(4):463-7), or 4-5 antigen (Krause P, et al., J Immunol Methods. 2003 December; 283 (1-2):261-7). However, the invention is not intended to be limited to the detection of autoantibodies to these particular tumour markers.

Assay methods according to the invention based on detection of anti tumour-marker autoantibodies (in single marker or panel assay form) may be employed in a variety of different clinical situations. In particular, the method may be used in the detection or diagnosis of cancer, in assessing the prognosis of a patient diagnosed with cancer, in predicting response to therapy, in monitoring the progress of cancer or other neoplastic disease in a patient, in detecting early neoplastic or early carcinogenic change in an asymptomatic human subject, in screening a population of asymptomatic human subjects in order either to identify those subjects who are at increased risk of developing cancer or to diagnose the presence of cancer, in predicting the response of a cancer patient to anti-cancer treatment (e.g. vaccination, anti-growth factor or signal transduction therapies, radiotherapy, endocrine therapy, human antibody therapy, chemotherapy), in monitoring the response of a cancer patient to anti-cancer treatment (e.g. vaccination, anti-growth factor or signal transduction therapies, radiotherapy, endocrine therapy, human antibody therapy chemotherapy), in the detection of recurrent disease in a patient previously diagnosed as having cancer who has undergone anti-cancer treatment to reduce the amount of cancer present, or in the selection of an anti-cancer therapy (e.g. vaccine, anti-growth factor or signal transduction therapies, radiotherapy, endocrine therapy, human antibody treatment chemotherapy), for use in a particular patient.

The inventors have generally observed that levels of cancer-associated autoantibodies show a positive correlation with disease state (see also WO 99/58979, the contents of which are incorporated herein by reference). Hence, when the method of the invention is used in clinical applications increased levels of anti-tumour marker autoantibodies, as compared to suitable controls, are generally taken as an indication of the cancer disease state.

For example, when the immunoassays are used in the diagnosis of cancer, the presence of an elevated level of autoantibodies, as compared to "normal" control individuals, is taken as an indication that the individual has cancer. The "normal" control individuals will preferably be age-matched controls not having any diagnosis of cancer based on clinical, imaging and/or biochemical criteria.

When the immunoassays are used in predicting the response of a cancer patient to anti-cancer treatment (e.g. vaccination, anti-growth factor or signal transduction, therapies, radiotherapy, endocrine therapy, human antibody therapy, chemotherapy), the presence of an elevated level of autoantibodies, as compared to "normal" control individuals, may be taken as an indication of whether or not the individual is likely to respond to the anti-cancer treatment. The "normal" control individuals will preferably be age-matched controls not having any diagnosis of cancer based on clinical, imaging and/or biochemical criteria. For each of the treatments listed above, a relationship between the level of autoantibodies compared to controls and likely success of treatment can be established by observation of the outcome of such treatment in patients whose autoantibody status is monitored throughout treatment. The previously established relationship may then be used to predict the likelihood success for each treatment in a given patient based on assessment of autoantibody status.

When the immunoassays are used in monitoring the progress of cancer or other neoplastic disease in a patient, the presence of an elevated level of autoantibodies, as compared to a "normal control", is taken as an indication of the presence of cancer in the patient. The "normal control" may be levels of autoantibodies present in control individuals, preferably age-matched, not having any diagnosis of cancer based on clinical, imaging and/or biochemical criteria. Alternatively, the "normal control" may be a "base-line" level established for the particular patient under test. The "base-line" level may be, for example, the level of autoantibodies present when either a first diagnosis of cancer or a diagnosis of recurrent cancer was made. Any increase above the base-line level would be taken as an indication that the amount of cancer present in the patient has increased, whereas any decrease below the baseline would be taken as an indication that the amount of cancer present in the patient has decreased. The "base-line" value may also be, for example, the level before a new treatment is commenced. A change in the level of autoantibodies would be taken as an indication of the effectiveness of the therapy. The direction of the "change" (i.e. increase vs decrease) indicating a positive response to treatment will be dependent upon the precise nature of the treatment. For any given treatment the direction of the "change" in autoantibody levels indicating a positive result may be readily determined, for example by monitoring autoantibody levels in comparison to other clinical or biochemical indicators of response to the treatment.

When the immunoassays are used in screening a population of asymptomatic human subjects this may be to identify those subjects who are at increased risk of developing cancer, individuals having an elevated level of autoantibodies, as compared to "normal" control individuals, are identified as being "at risk" of developing cancer. The "normal" control individuals will preferably be age-matched controls not identified as having any predisposition to developing cancer or any significant elevated risk of developing cancer. An exception to this may be where age itself is a major risk factor.

When the immunoassays are used in screening a population of asymptomatic human subjects this may be to diagnose cancer in those subjects who have already developed a cancer, individuals having an elevated level of autoantibodies as compared to "normal" control individuals being scored as having cancer or some form of neoplastic change. The "normal" control individuals will preferably be age-matched controls not identified as having any predisposition to developing cancer or any significant elevated risk of developing cancer. An exception to this may be where age itself is a major risk factor. Alternatively, the "normal control" may be a "base-line" level established for the particular patient under test. The "base-line" level may be, for example, the level of autoantibodies present when the patient was first tested and found to have levels not elevated above a "normal control" population. Any increase thereafter against this baseline measurement would be taken as an indication of the presence of cancer in that individual. Thus the individual could through such a baseline test become their own control for future autoantibody measurement.

When the immunoassays are used in monitoring the response of a cancer patient to anti-cancer treatment (e.g. vaccination, anti-growth factor or signal transduction therapies, radiotherapy, endocrine therapy, human antibody therapy, chemotherapy), the presence of an altered level of autoantibodies after treatment is taken as an indication that the patient has responded positively to the treatment. A baseline level of autoantibodies taken before treatment is commenced may be used for comparison purposes in order to determine whether treatment results in an "increase or decrease" in autoantibody levels. A change in the level of autoantibodies would be taken as an indication of the effectiveness of the therapy. The direction of the "change" (i.e. increase vs decrease) indicating a positive response to treatment will be dependent upon the precise nature of the treatment. For any given treatment the direction of the "change" in autoantibody levels indicating a positive result may be readily determined, for example by monitoring autoantibody levels in comparison to other clinical or biochemical indicators of response to the treatment.

The method of the invention may used in predicting and/or monitoring response of an individual to essentially any known anti-cancer treatment. This includes, for example human antibody therapy wherein monoclonal or polyclonal antibodies are infused into the patient, a non-limiting specific example being treatment with the anti-growth factor antibody Herceptin™ (Baselga, J., D. Tripathy et al., J Clin Oncol., 14(3), 737-744, 1996). The presence of a natural autoantibody response may enhance or inhibit the effectiveness of treatment with artificially infused therapeutic antibodies. Using the method of the invention it is possible to correlate response to any anti-cancer treatment, including antibody therapy, with natural levels of autoantibodies prior to and over the course of the treatment in any patient or group of patients. This knowledge may then in turn be used to predict how other patients (or the same patient in the case of repeated treatment) will respond to the same treatment.

When the immunoassays are used in detection of recurrent disease, the presence of an increased level of autoantibodies in the patient, as compared to a "normal control", is taken as an indication that disease has recurred. The "normal control" may be levels of autoantibodies present in control individuals, preferably age-matched not having any diagnosis of cancer based on clinical, imaging and/or biochemical criteria. Alternatively, the "normal control" may be a "base-line" level established for the particular patient under test. The "base-line" level may be, for example, the level of autoantibodies present during a period of remission from disease based on clinical, imaging and/or biochemical criteria.

The assay method of the invention may be applied in the detection of many different types of cancer, of which examples are breast, bladder, colorectal, prostate, lung, pancreatic and ovarian cancers. The assays may complement existing methods of screening and surveillance. For example, in the case of primary breast cancer immunoassays for autoantibodies could be used to alert clinicians to biopsy small lesions on mammograms which radiographically do not appear suspicious or to carry out breast imaging or to repeat imaging earlier than planned. In the clinic, the assay methods of the invention are expected to be more objective and reproducible compared to current imaging techniques (i.e. mammography and ultrasound), the success of which can be operator-dependent.

"Panel assays" may be tailored having regard to the particular clinical application. A panel of antigens for detection of autoantibodies to at least p53 and c-erbB2 is particularly useful for many types of cancer and can optionally be supplemented with other markers having a known association with the particular cancer, or a stage of the particular cancer, to be detected. For example for breast cancer the panel might include MUC 1 and/or c-myc and/or BRCA1 and/or BRCA2 and/or PSA whereas bladder cancer the panel might optionally include MUC 1 and/or c-myc, for colorectal cancer ras and/or APC, for prostate cancer PSA and/or BRCA1 and/or BRCA2 or for ovarian cancer BRCA1 and/or BRCA2 and/or CA125. There are other preferred embodiments in which p53 or c-erbB2 are not necessarily essential.

In the case of breast cancer suitable panels could be selected from the following:
p53 and MUC 1 with optional c-erbB2 and/or c-myc, and/or BRCA1 and/or BRCA2 and/or PSA and/or NY-ESO-1 and/or BRC1;
p53 and c-myc with optional c-erbB2 and/or MUC1 and/or BRCA1 and/or BRCA2 and/or PSA and/or NY-ESO-1 and/or BRC1;
p53 and BRCA1 with optional c-erB2 and/or MUC 1 and/or c-myc and/or BRCA2 and/or PSA and/or NY-ESO-1 and/or BRC1;
p53 and BRCA2 with optional c-erbB2 and/or MUC 1 and/or c-myc and/or BRCA1 and/or PSA and/or NY-ESO-1 and/or BRC1;
c-erbB2 and MUC 1 with optional p53 and/or c-myc, and/or BRCA1 and/or BRCA2 and/or PSA and/or NY-ESO-1 and/or BRC1;
c-erbB2 and c-myc with optional p53 and/or MUC 1 and/or BRCA1 and/or BRCA2 and/or PSA and/or NY-ESO-1 and/or BRC1;
c-erbB2 and BRCA1 with optional p53 and/or MUC 1 and/or c-myc and/or BRCA2 and/or PSA and/or NY-ESO-1 and/or BRC1;
c-erbB2 and BRCA2 with optional p53 and/or MUC 1 and/or c-myc and/or BRCA1 and/or PSA;
p53, c-myc, NY-ESO-1 and BRCA2.

In the case of colorectal cancer suitable panels could be selected for example from the following:
p53 and ras with optional c-erbB2 and/or APC;
p53 and APC with optional c-erbB2 and/or Ras;
Ras and APC with optional p53 and/or c-erbB2
Such panels might also include CEA or CA19-9.

In the case of prostate cancer suitable panels could be selected for example from the following:
p53 and PSA with optional BRCA1 and/or BRCA2 and/or c-erbB2;
c-erbB2 and PSA with optional p53 and/or BRCA1 and/or BRCA2;
PSMA, PSCA and kallikreins.

In the case of ovarian cancer suitable panels could be selected for example from the following:
p53 and CA125 with optional c-erbB2 and/or BRCA1 and/or BRCA2;
c-erbB2 and CA125 with optional p53 and/or BRCA1 and/or BRCA2;
HER2, annexins, CAGE and 4-5.

In the case of lung cancer suitable panels may be selected from:
p53 and NY-ESO-1, optionally with further markers;
HER2, annexins, CAGE and 4-5.

Where the method of the invention is used to perform a "panel assay" based on two or more tumour marker antigens derived from different proteins, at least one of the antigens in the panel must be tested in an assay according to the invention based on testing of multiple different amounts of the antigen to form a titration curve. Preferably each of the antigens forming the panel is tested according to the assay of the invention and a titration curve plotted/calculated for each individual antigen in the panel.

The invention also contemplates that a titration assay for detection of at least one anti-tumour marker antibody may be used in combination with an assay designed to detect at least one tumour marker protein (which may be related or unrelated to the antigen used in the titration assay) in the same patient sample. Thus assays for anti-tumour marker autoantibodies and assays for tumour marker proteins may be performed in parallel on a single patient sample.

In a further embodiment, the immunoassay method of the invention may be used in the selection of an anti-cancer vaccine for use in a particular patient. In this embodiment a sample of bodily fluid taken from the patient is tested using a panel of two or more antigens, each corresponding to a different tumour marker protein, in order to determine the relative strength of the patient's immune response to each of the different tumour marker proteins. The "strength of immune response" to a given tumour marker protein or proteins is indicated by the presence and/or the amount of cancer-associated autoantibodies specific to that tumour marker protein detected using the immunoassay; where autoantibodies are quantified, the greater the level of cancer-associated autoantibodies, the stronger the immune response. The tumour marker protein or proteins identified as eliciting the strongest immune response or strong responses in the patient (i.e. the highest level of autoantibodies) is or are then selected to form the basis of an anti-cancer vaccine for use in the patient.

The utility of the method of the invention is not limited to detection of anti-tumour autoantibodies, although the assay is particularly useful for this purpose. Cancer is just one example of a disease wherein detection of autoantibodies may be used as a biological marker for disease state/disease susceptibility. The inventors have shown that substantial advantages are gained by the use of a titration approach to detect autoantibodies in patient samples. It is therefore reasonable to conclude that similar advantages will be gained by the use of the titration approach to detect autoantibodies that are biological markers for diseases other than cancer. The method is therefore applicable to detection of any autoantibody which serves as a biological marker for a disease state or disease susceptibility, in any disease which has been shown (or can be shown) to be associated with autoantibody production.

Other applications of the method of the invention include, but are not limited to, detection of autoantibodies that are biological markers of autoimmune disease, such as for example rheumatoid arthritis, systemic lupus erythematous (SLE), primary biliary cirrhosis (PBC), autoimmune thyroiditis (e.g. Hashimoto's thyroiditis), autoimmune gastritis (e.g. pernicious anaemia), autoimmune adrenalitis (e.g. Addison's disease), autoimmune hypoparathyroidism, autoimmune diabetes (e.g. Type 1 diabetes) or myasthenia gravis and screening of patient samples for kidney or hepatic disease leading to insufficiency or failure of either organ, and for screening of patient samples post-transplantation to detect the presence of antibodies directed against either the diseased tissue (which has been left in-situ post-transplantation) or against the transplanted tissue.

In a further aspect the invention relates to a method of detecting an antibody in a test sample comprising a bodily fluid from a mammalian subject, wherein said antibody is directed to a foreign substance introduced into said mammalian subject, the method comprising:
(a) contacting the test sample with a plurality of different amounts of an antigen specific for said antibody,
(b) detecting the amount of specific binding between said antibody and said antigen, and
(c) plotting or calculating a curve of the amount of said specific binding versus the amount of antigen for each amount of antigen used in step (a).

Preferably, in this embodiment of the invention the method includes as step (d) detecting the presence of said antibody based upon the amount of specific binding between said antibody and said antigen at each different antigen concentration used, in other words the collective values observed for a particular antigen. Preferably, the presence in the test sample of antibody reactive with the antigen used in the assay is indicated by a generally S-shaped or sigmoidal curve.

In this aspect of the invention the titration methodology may be used to evaluate the immune response of a mammalian subject, and preferably a human subject, to any foreign substance introduced into said subject.

In one embodiment the foreign substance may be a therapeutic agent, such as for example a drug or prodrug, human antibody therapy or vaccine. The method of the invention may be used to assess whether administration of a therapeutic agent to a patient triggers an immune response leading to the production of antibodies specific for an epitope on the therapeutic agent, or a component of a delivery vehicle, excipient, carrier etc. administered with the therapeutic agent.

The precise nature of the therapeutic agent is not limiting to the invention. In non-limiting embodiments the method of the invention may be used to assess immune response to synthetic small molecules, naturally occurring substances, naturally occurring or synthetically produced biological agents, or any combination of two or more of the foregoing, optionally in combination with excipients, carriers or delivery vehicles.

In one useful embodiment the method of the invention may be used to assess the immune response to a non-target portion of a therapeutic agent or vaccine. By "non-target" portion is meant a component part of the administered therapeutic agent or vaccine which, in the case of a therapeutic agent, does not contribute directly to therapeutic activity or, in the case of a vaccine, is not intended to elicit production of antibodies in the host.

The non-target portion may be present, for example, to facilitate purification of the therapeutic agent or vaccine or may be designed to assist with delivery, uptake or targeting of the therapeutic agent/vaccine. Examples of such "non-target" portions include, but are not limited to linkers or makers commonly attached to recombinantly expressed polypeptides such as biotin labels, histidine tags etc.

In another embodiment of this aspect of the invention, the foreign substance may be an infectious agent, such as fungus, bacteria, virus or parasite.

The invention will be further understood with reference to the following non-limiting experimental examples:

Example 1

General Protocol for Titration of Antigen in an Autoantibody Assay

Samples of (biotinylated) tumour marker antigens may be prepared by recombinant expression, following analogous methods to those described in WO 99/58978.

Briefly, cDNAs encoding the marker antigens of interest were cloned into the pET21 vector (Invitrogen) which has been modified to encode a biotin tag and a 6× histidine tag to aid in purification of the expressed protein. The resulting clones are grown in a suitable bacterial host cell (in inclusion bodies), the bacteria lysed and denatured and the expressed antigens recovered via Nickel chelate affinity columns-(Hi-trap, commercially available from Amersham, following manufacturer's protocol). The expressed antigens were renatured by dialysis in appropriate buffer and the yield of expressed protein assessed by SDS-PAGE, western blot and ELISA and quantitated prior to storage.

The negative control VOL is empty vector (i.e. no cloned cDNA) which still includes the His and biotin tag sequences)

GenBank accession numbers for a number of marker cDNAs are as follows:

P53: B003596
c-myc: V00568
ECD6 (HER2) extracellular domain: M11730
NY-ESO: NM_001327
BRCA2: U43746
BRCA1 delta 9-10: NM_007302

1. Antigens and VOL (negative control) were diluted to appropriate concentrations in 0.1 M carbonate buffer then diluted serially to form a semi-log titration range (see table 1). Antigen dilutions were dispensed at 50 µl/well into the rows of a Falcon micotitre plate according to plate layout using an electronic multi-channel pipette. Plates were covered and stored at 4° C. for 48 h.

2. Plates were washed once in PBS+0.1% tween 20 using an automated plate washer then tapped dry on tissue paper.

3. Plates were blocked with high salt incubation buffer (HSB, PBS+0.5M NaCl+0.1% casein) at 200 µl/well for one hour or until required for use (store covered at 4° C.).

4. Serum samples were defrosted, vortexed and diluted 1/100 in HSB at room temp.

5. Plates were emptied and tapped dry on tissue paper. Each diluted serum sample was dispensed at 50 µl/well into all wells of the microtitre plate using an electronic multi-channel pipette. Control antibodies were diluted 1/1000 in HSB and dispensed into appropriate wells of plate final plate. Plates covered and incubated for 1.5 hour at room temp with shaking.

6. Wash step: Plates were washed three times in PBS+0.1% tween 20 using an automated plate washer then tapped dry on tissue paper.

7. Horseradish peroxidase conjugated rabbit anti-human Ig (Jackson, 1/10,000 in HSB) was dispensed at 50 µl/well into all wells of the microtitre plate. HRP-conjugated rabbit anti-mouse Ig (1/1000 in HSB) was dispensed into control wells containing anti-antigen antibody. Plates were then incubated at room temp for 1 hour with shaking.

8. Plates were washed as in step 6.

9. Pre-prepared TMB substrate was added at 50 µl/well and plate incubated on bench for 10 min. Plates were gently tapped to mix.

10. Optical density of wells was determined at 650 nm using a standard plate reader protocol.

Example 2

Detection of Autoantibodies in Primary Breast Cancer

The following data were obtained from a pilot study to assess the sensitivity and reproducibility of a panel of titration autoantibody assays in primary breast cancer (PBC). The study included serum from 17 women with no evidence of cancer and pre-operative serum samples from 20 women with primary breast cancer. Normal and cancer samples were age matched. One normal and three cancer samples had to be removed from the study because they showed evidence of anti-biotin antibody responses and therefore could not be assessed using the assay in its present format. Approximately 10% of the population is thought to develop an immune response against biotin.

The assay was carried out according to the protocol given in example 1 using the antigens p53, c-myc, NY-ESO-1 and BRCA2

FIG. 1 gives examples of curves obtained when the antigen titration assay was used to measure p53 autoantibodies in serum. It can be seen that the cancer patient's serum 17766(C) binds strongly to the test antigen (p53) with a characteristic sigmoidal curve but does not bind to the negative control, VOL. In comparison, serum from a normal individual, 18052 (N) does not give a titration curve for binding to the test antigen or the negative control.

Figure 2:
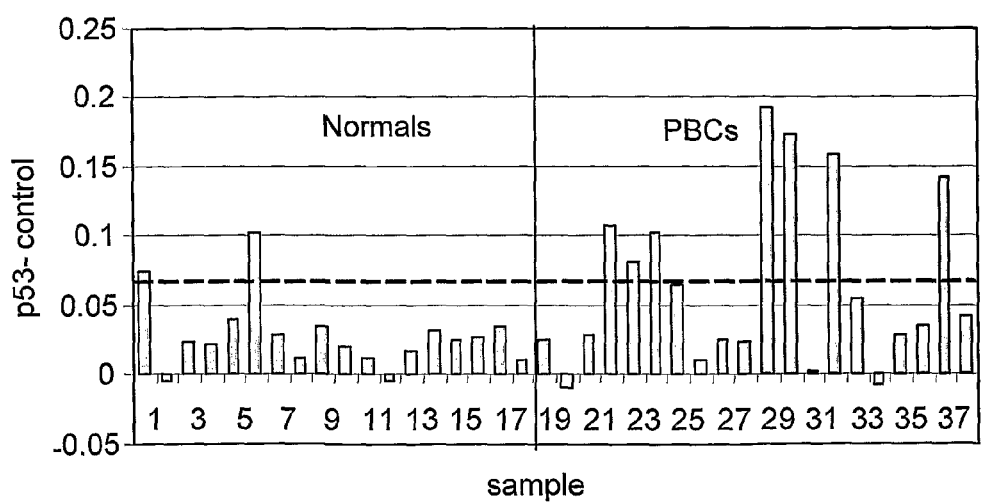
FIG. 2: Comparison of p53 autoantibody levels in normal individuals and patients with primary breast cancer (PBC) as measured using the antigen titration assay. Autoantibody levels are expressed as the $OD_{650}$ due to binding to the test antigen (p53) minus that due to binding to the negative control. Normal cut-off (-----) was calculated as the mean plus 2 standard deviations of the normal population.

Autoantibody levels were expressed as the optical density (650 nm) due to binding to the test antigen minus that due to binding to the negative control (VOL). The normal cut-off was calculated as the 95th percentile (mean+2 standard deviations) of the normal group. This is shown as the dotted line in FIG. 2, in which anti-p53 autoantibody levels in normal individuals are compared with cancer patients. It can be seen that the cancer group show generally higher autoantibody levels and also have a greater proportion of individuals with levels above cut-off.

The panel consisted of four antigens; p53, c-myc, NY-ESO-1 and BRCA2. The sensitivity of the individual assays is given in table 2 along with the combined sensitivity of the panel of four antigens in the detection of primary breast cancer (63%).

TABLE 1 standard plate layouts

| | 1 | 2 | 3 | 4 | 5 | 6 | 7 | 8 | 9 | 10 | 11 | 12 |
|---|---|---|---|---|---|---|---|---|---|---|---|---|
| | | | | | | P53 plates | | | | | | |
| A | p53 10 µg/ml | | | c-myc 10 µg/ml | | | NY-ESO 10 µg/ml | | | VOL 10 µg/ml | | |
| B | p53 3 µg/ml | | | c-myc 3 µg/ml | | | NY-ESO 3 µg/ml | | | VOL 3 µg/ml | | |
| C | p53 1 µg/ml | | | c-myc 1 µg/ml | | | NY-ESO 1 µg/ml | | | VOL 1 µg/ml | | |
| D | p53 0.3 µg/ml | | | c-myc 0.3 µg/ml | | | NY-ESO 0.3 µg/ml | | | VOL 0.3 µg/ml | | |
| E | p53 0.1 µg/ml | | | c-myc 0.1 µg/ml | | | NY-ESO 0.1 µg/ml | | | VOL 0.1 µg/ml | | |
| F | p53 0.03 µg/ml | | | c-myc 0.03 µg/ml | | | NY-ESO 0.03 µg/ml | | | VOL 0.03 µg/ml | | |
| G | p53 0.01 µg/ml | | | c-myc 0.01 µg/ml | | | NY-ESO 0.01 µg/ml | | | VOL 0.01 µg/ml | | |
| H | carbonate buffer | | | carbonate buffer | | | carbonate buffer | | | carbonate buffer | | |
| | | | | | | BRCA plates | | | | | | |
| A | BRCA1 10 µg/ml | | | BRCA2 10 µg/ml | | | ECD-6 10 µg/ml | | | VOL 10 µg/ml | | |
| B | BRCA1 3 µg/ml | | | BRCA2 3 µg/ml | | | ECD-6 3 µg/ml | | | VOL 3 µg/ml | | |
| C | BRCA1 1 µg/ml | | | BRCA2 1 µg/ml | | | ECD-6 1 µg/ml | | | VOL 1 µg/ml | | |
| D | BRCA1 0.3 µg/ml | | | BRCA2 0.3 µg/ml | | | ECD-6 0.3 µg/ml | | | VOL 0.3 µg/ml | | |
| E | BRCA1 0.1 µg/ml | | | BRCA2 0.1 µg/ml | | | ECD-6 0.1 µg/ml | | | VOL 0.1 µg/ml | | |
| F | BRCA1 0.03 µg/ml | | | BRCA2 0.03 µg/ml | | | ECD-6 0.03 µg/ml | | | VOL 0.03 µg/ml | | |
| G | BRCA1 0.01 µg/ml | | | BRCA2 0.01 µg/ml | | | ECD-6 0.01 µg/ml | | | VOL 0.01 µg/ml | | |
| H | carbonate buffer | | | carbonate buffer | | | carbonate buffer | | | carbonate buffer | | |

TABLE 2

Sensitivity of the antigen titration autoantibody assay.

| p53 | c-myc | NY-ESO-1 | BRCA2 | Panel |
|---|---|---|---|---|
| 6/17 (35%) | 5/17 (29%) | 4/17 (24%) | 4/17 (24%) | 63% |

Autoantibodies against four different antigens were measured and the combined sensitivity of the panel calculated. Cut-off levels were calculated as mean + 2 standard deviations of the normal sample set. Individuals with anti-biotin antibody responses were excluded as not capable of assessment.

In order to assess whether or not the measurements obtained using the titration autoantibody assay were reproducible, assays were performed on three separate days and the results are shown in table 3. An assay was deemed to be reproducible if all three results agreed. Reproducibility of measurements made on normal serum was 94% (15/16) and 88% (14/16) in breast cancer samples.

TABLE 3

Reproducibility of the antigen titration assay for p53 autoantibodies.

| Normals | Run A | Run B | Run C | PBCs | Run A | Run B | Run C |
|---|---|---|---|---|---|---|---|
| 18017 | − | + | + | 17733 | + | − | − |
| 18018 | − | − | − | 17734 AB | + | − | − |
| 18019 | − | − | − | 17735 | − | − | − |
| 18020 | − | − | − | 17742 | + | + | + |
| 18021 | − | − | − | 17743 | + | + | + |
| 18047 | − | − | − | 17744 | + | + | + |
| 18048 AB | + | − | + | 17755 | − | + | − |
| 18049 | − | − | − | 17756 | − | − | − |
| 18050 | ND | − | − | 17757 | − | − | − |
| 18051 | − | − | − | 17758 | ND | − | − |
| 18052 | − | − | − | 17759 | + | + | + |
| 18053 | − | − | − | 17766 | + | + | + |
| 18054 | − | − | − | 17774 | − | − | − |
| 18055 | − | − | − | 17775 AB | + | + | − |
| 18056 | − | − | − | 17776 | − | − | − |
| 18057 | − | − | − | 17777 | − | − | ND |
| 18058 | − | − | − | 17796 | − | − | − |
|  |  |  |  | 17797 AB | + | − | − |
|  |  |  |  | 17832 | + | + | + |
|  |  |  |  | 17450 | − | − | − |

Assays were performed on three separate days (Runs A, B and C) on serum samples from patients with primary breast cancer (PBC) or normal controls. Cut-off levels were calculated on a daily basis as mean + 2 standard deviations of the normal sample set. AB denotes individuals that showed evidence of an anti-biotin antibody response and whom can not be assessed by the present assay format. An assay was deemed to be reproducible if all three results agreed. Reproducibility of the normal individuals was 94% (15/16) and the PBC patients was 88% (14/16).

Example 3

Detection of Autoantibodies in Lung Cancer

Figure 3:
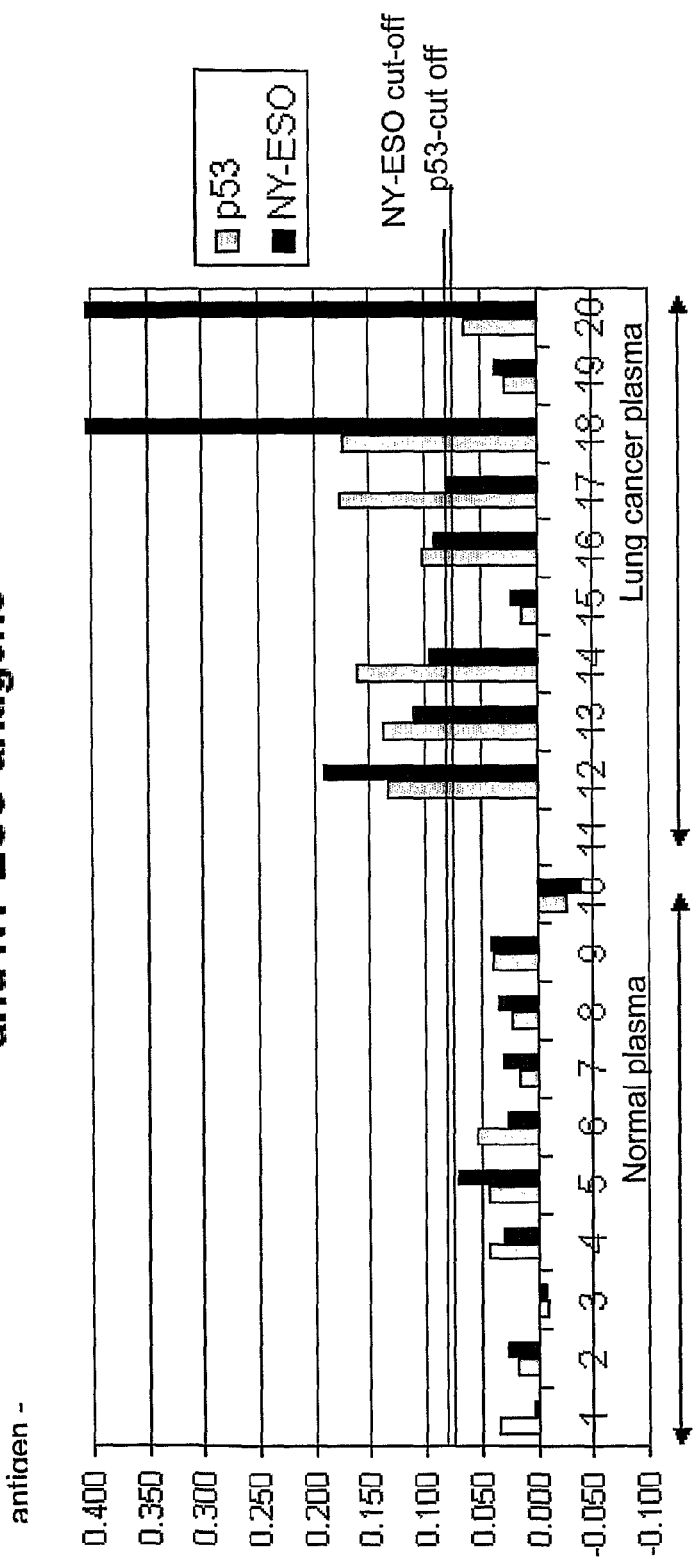
FIG. 3 shows a comparison of p53 and NY-ESO autoantibody levels in normal individuals and patients with lung cancer as measured using the antigen titration assay. Autoantibody levels are expressed as the $OD_{650}$ due to binding to the test antigen (p53 or NY-ESO) minus that due to binding to the negative control. Normal cut-offs (-----) were calculated as the mean plus 2 standard deviations of the normal population.

Analysis of autoantibody responses against 2 antigens (p53 and NY-ESO) in a pilot lung cancer study (10 normal and 9 lung cancer plasma) revealed a detection rate of 78% (FIG. 3).

The assay was carried out according to the general protocol of example 1, except that plasma samples were used instead of serum.

Positive patient samples exhibited sigmoidal titration curves similar to that shown in FIG. 1. FIG. 3 shows a comparison of p53 and NY-ESO autoantibody levels in normal individuals and patients with lung cancer as measured using the antigen titration assay. Normal cut-offs were calculated as the mean plus 2 standard deviations of the normal population.

Example 4

Additional Titration Curves

The following additional titration curves were all generated in assays based on the general methodology described in Example 1. The results indicate that the titration curve approach may be applied to detection of a variety of different antigens, in different types of bodily fluids and in different disease (exemplified by different types of cancer) and also illustrate the advantage of the method of the invention in distinguishing between "true" and "false" positive results.

Figure 4:
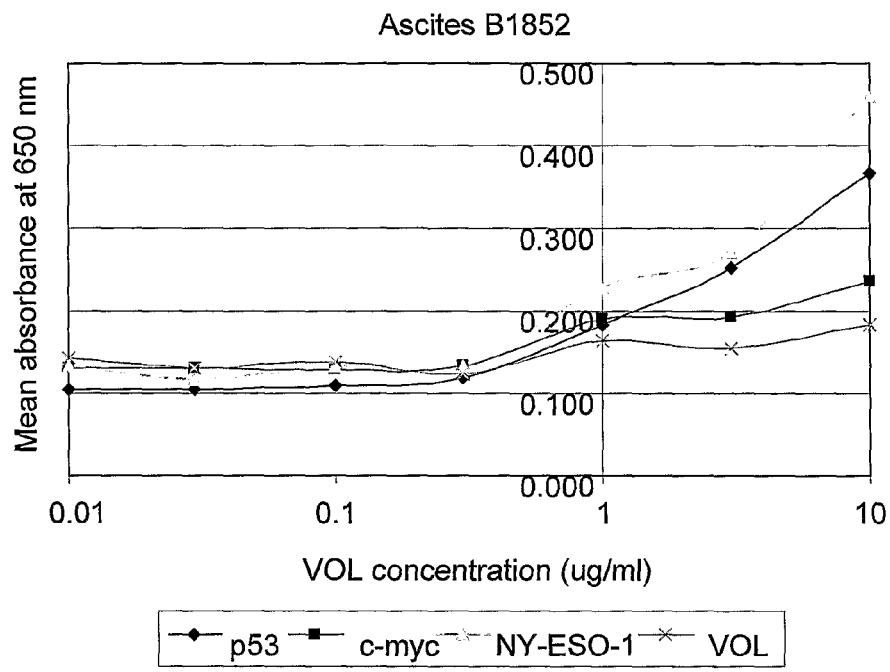
FIG. 4 shows a titration curve for detection of autoantibodies against p53 and NY-ESO in a sample of ascites fluid taken from a patient with breast cancer. This patient was tested but found not to produce autoantibodies against c-myc.

FIG. 4 shows a titration curve for detection of autoantibodies against p53 and NY-ESO in a sample of ascites fluid taken from a patient with breast cancer. This patient was tested but found not to produce autoantibodies against c-myc.

Figure 5:
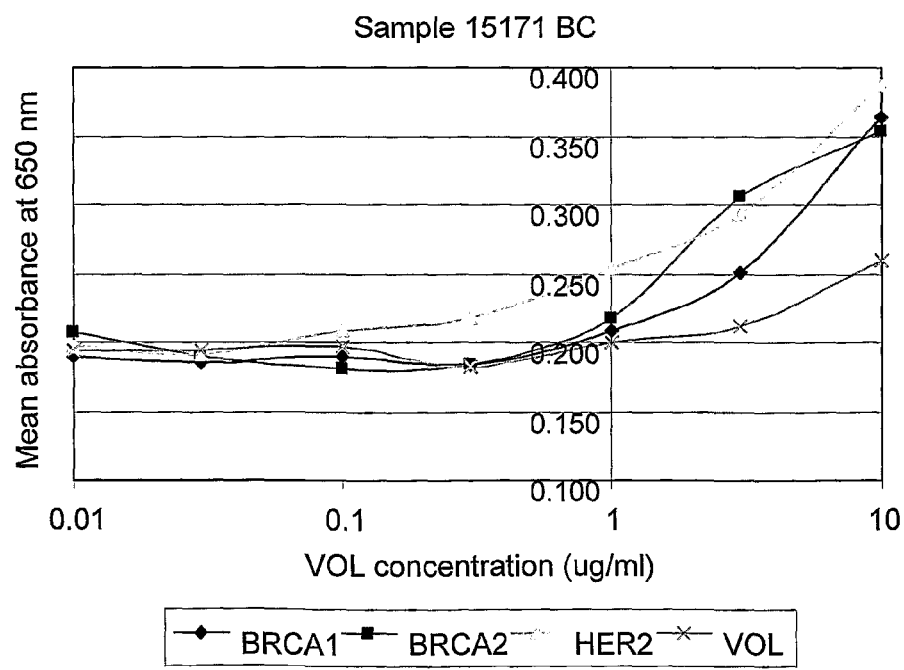
FIG. 5 shows a titration curve for detection of autoantibodies against BRCA1, BRCA2 and HER2 in a sample of serum from a patient with breast cancer (ductal carcinoma in situ).

FIG. 5 shows a titration curve for detection of autoantibodies against BRCA1, BRCA2 and HER2 in a sample of serum from a patient with breast cancer (ductal carcinoma in situ).

Figure 6:
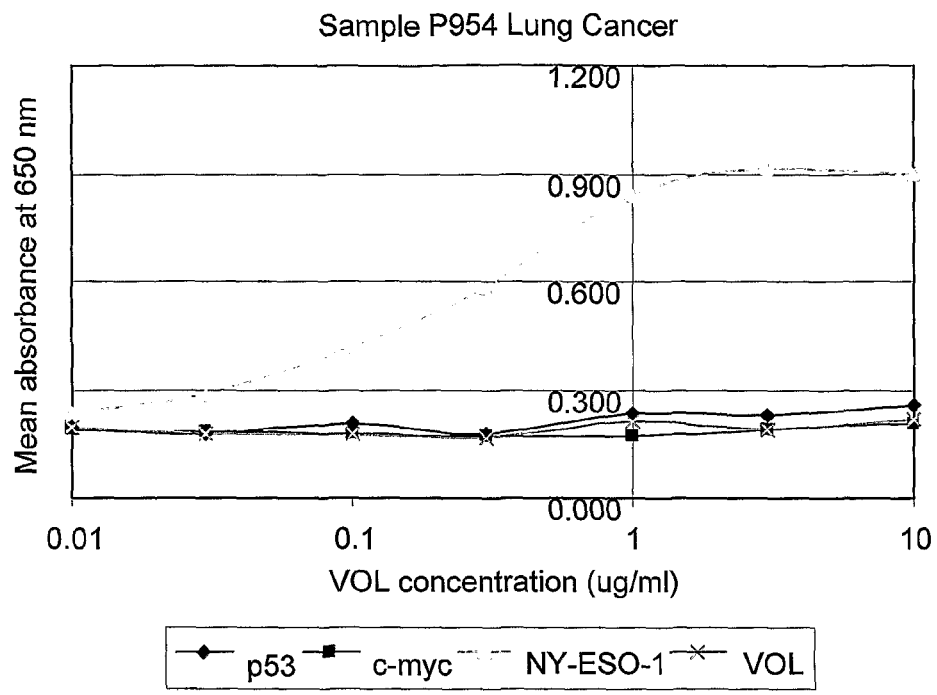
FIG. 6 shows a titration curve for detection of autoantibodies against NY-ESO in a sample of serum from a patient with lung cancer. This patient was tested but found not to produce autoantibodies against p53 or c-myc.

FIG. 6 shows a titration curve for detection of autoantibodies against NY-ESO in a sample of serum from a patient with lung cancer. This patient was tested but found not to produce autoantibodies against p53 or c-myc.

Figure 7:
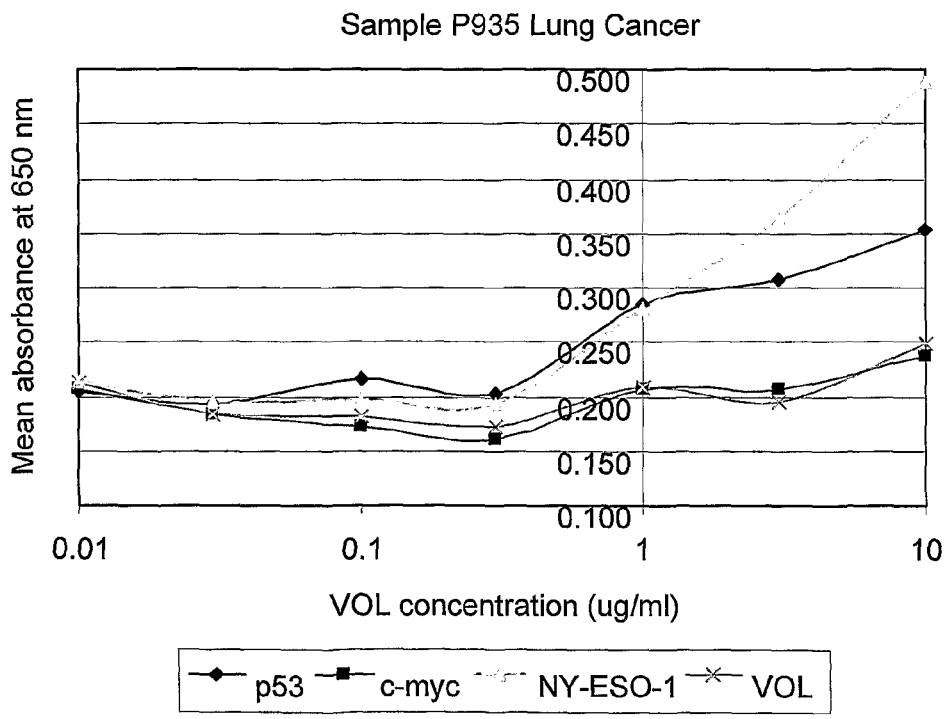
FIG. 7 shows a titration curve for detection of autoantibodies against NY-ESO and p53 in a sample of serum from a patient with lung cancer. This patient was tested but found not to produce autoantibodies against c-myc.

FIG. 7 shows a titration curve for detection of autoantibodies against NY-ESO and p53 in a sample of serum from a patient with lung cancer. This patient was tested but found not to produce autoantibodies against c-myc.

Figure 8A:
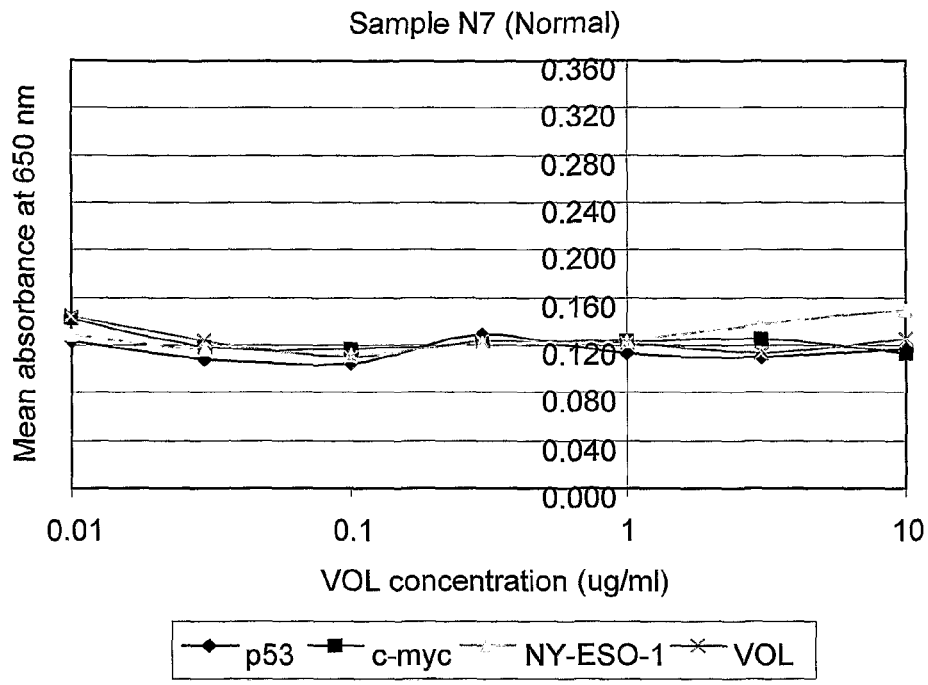
FIGS. 8(a) and 8(b) illustrate the results on two independent titration assays for autoantibodies against p53, c-myc and NY-ESO-1 in samples of serum from a "normal" subject (i.e. an individual with no evidence of cancer).
Figure 8B:
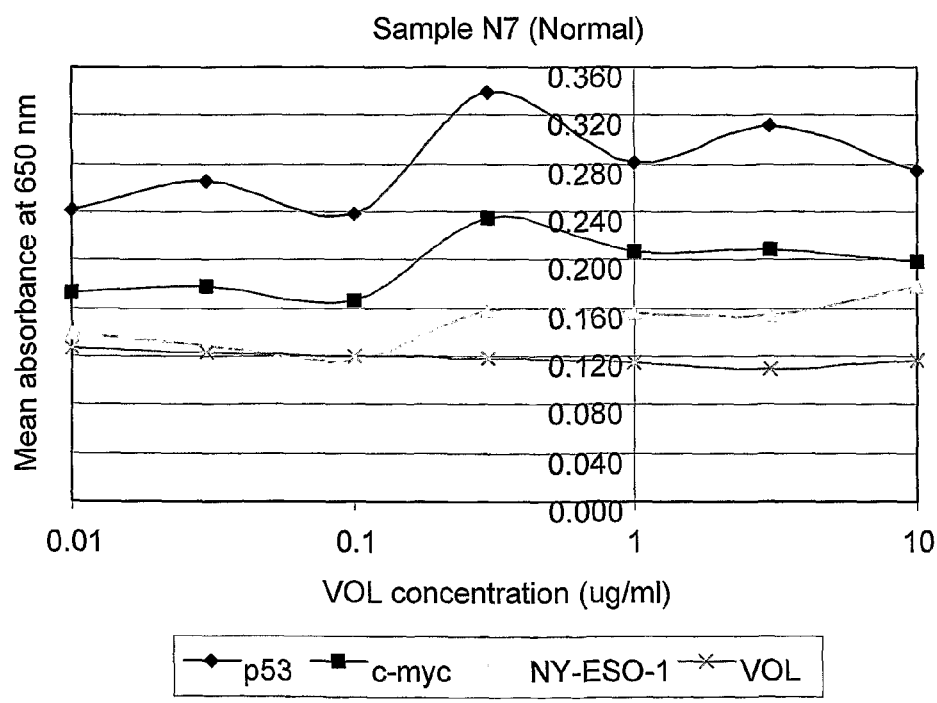

FIGS. 8(a) and 8(b) illustrate the results on two independent titration assays for autoantibodies against p53, c-myc and NY-ESO-1 in samples of serum from a "normal" subject (i.e. an individual with no evidence of cancer). In the assay shown in FIG. 8(a) a flat line is observed with increasing amounts of antigen, indicating that the serum sample does not contain autoantibodies to any of the tested antigens. When a second aliquot of the same patient serum sample was tested again using the same assay methodology the assay failed producing the anomalous results shown in FIG. 8(b). The absence of the characteristic titration curve with increasing amounts of antigen indicates that this is an anomalous result, rather than a true positive. Had this sample been tested in a single point assay using a single, fixed amount of antigen then it may have appeared as a "false positive" result. Thus, these results illustrate the advantage of the titration curve approach in distinguishing between true and false positive results.

Figure 9A:
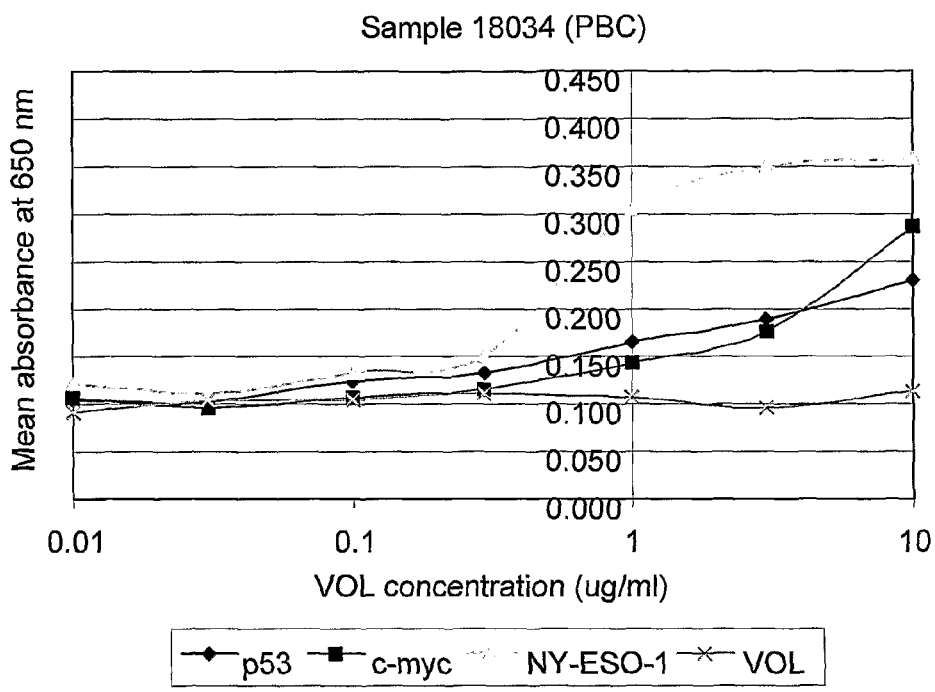
FIGS. 9(a) and 9(b) show the results of two independent titration assays carried out on samples of serum from a single patient with invasive breast cancer using a range of different antigens.
Figure 9B:
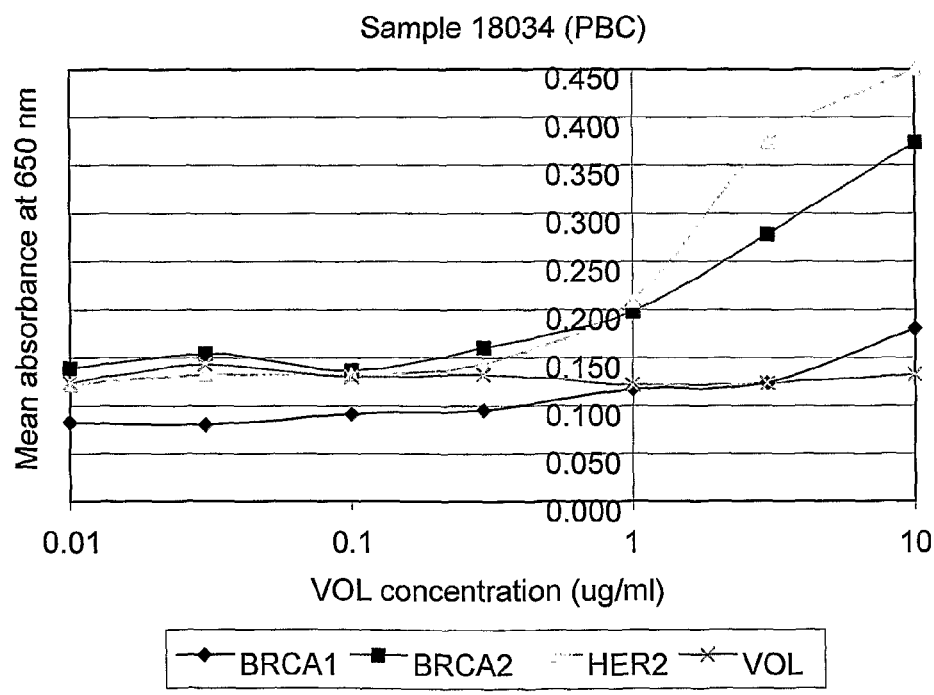

FIGS. 9(a) and 9(b) shows the results of two independent titration assays carried out on samples of serum from a single patient with invasive breast cancer using a range of different antigens. This particular patient shows autoantibodies to NY-ESO-1, HER2 and BRCA2. For each positive antigen a positive assay result is indicated by increasing signal strength as the concentration of antigen increases, i.e. a titrating signal.

Figure 10A:
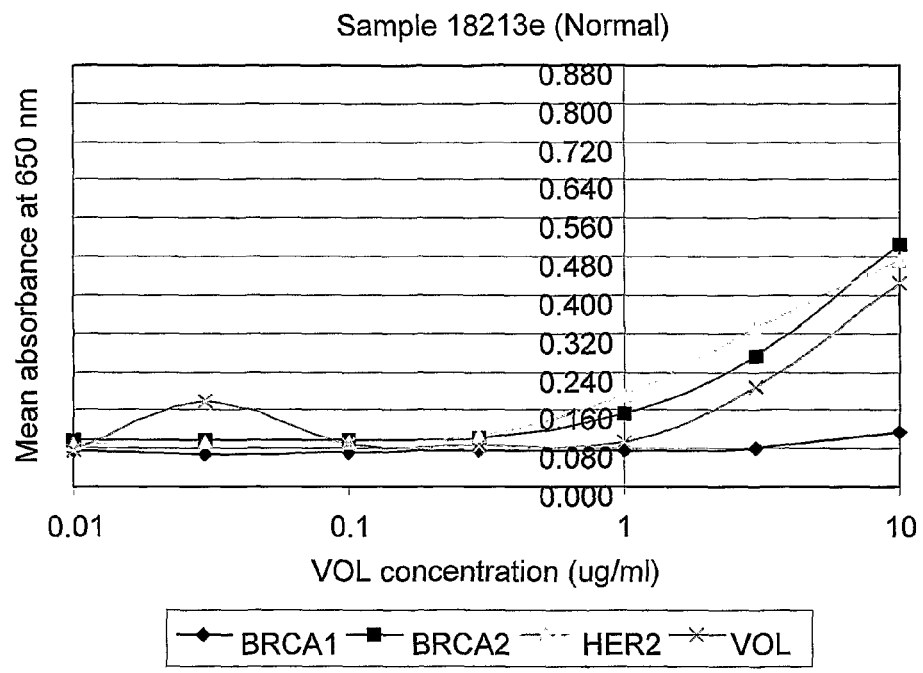
FIGS. 10(a) and 10(b) illustrate the results of titration assays in which samples of serum from a clinically normal human subject were tested for the presence of autoantibodies using biotinylated antigens BRCA2, HER2, c-myc and NY-ESO-1, non-biotinylated BRCA1 and control expression products of the "empty" vector VOL, which encodes the biotin tag but no additional antigen.
Figure 10B:
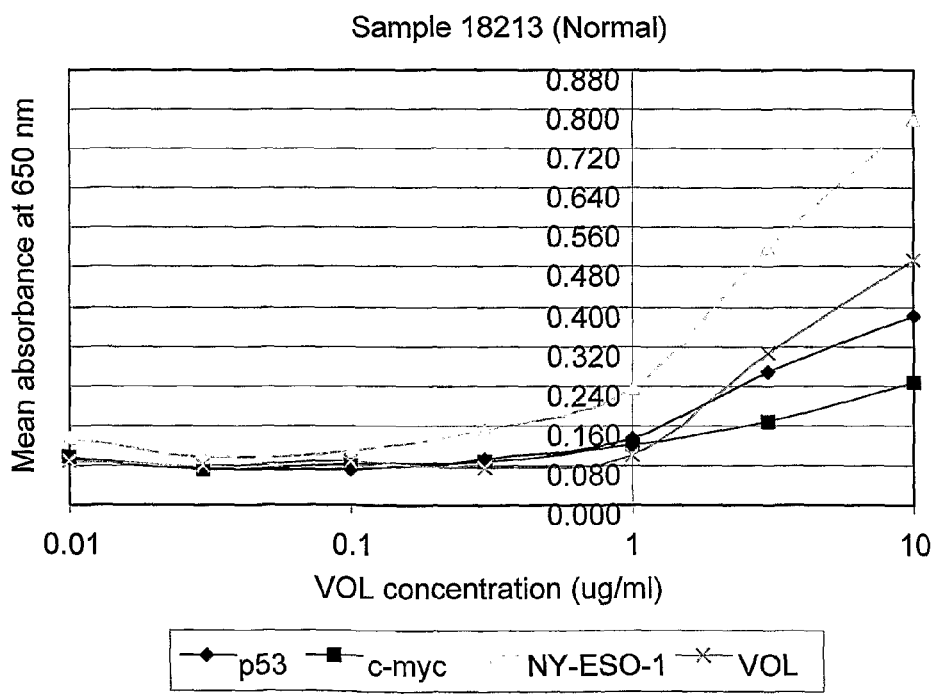

FIGS. 10(a) and 10(b) illustrate the utility of the invention in distinguishing between anti-biotin responses and "true" autoantibodies to a specific antigen (i.e. a tumour marker). In these assays samples of serum from a clinically normal human subject were tested for the presence of autoantibodies using biotinylated antigens BRCA2, HER2, c-myc and NY-ESO-1, non-biotinylated BRCA1 and control expression products of the "empty" vector VOL, which encodes the biotin tag but no additional antigen. The tested individual exhibits a titrating response to both biotinylated antigens and to the empty vector VOL, which is effectively biotin alone, but no response to the non-biotinylated antigen BRCA1, indicating that the "positive" results with the biotinylated markers are in fact due to the presence of anti-biotin antibodies in this individual.

Example 5

Analysis of the Sensitivity and Specificity of Antigen Titration Assays Compared with Single Point Measurement Autoantibody (AAb) measurements were performed on 100 women with primary breast-cancer (PBC) and 80 women with no evidence of malignant disease using both the titration method and by measuring at a single concentration of antigen (10 µg/ml). Tables showing a direct comparison of the two methods are shown below:

TABLE 4

Comparison of the-sensitivity of the titration AAb assay with a measurement at a single antigen concentration in PBC.

| Antigen | Single point | Titration assay |
|---|---|---|
| p53 | 17.5% | 18.9% |
| c-myc | 6.2% | 22.9% |
| NY-ESO-1 | 24.7% | 25.0% |
| BRCA2 | 20.6% | 31.3% |
| HER2 | 23.7% | 25.0% |
| MUC1 | 18.5% | 19.8% |
| Panel (of 6 Ags) | 54.6% | 62.2% |

TABLE 5

Comparison of the specificity of the titration AAb assay with a measurement at a single antigen concentration in normal women.

| Antigen | Single point | Titration assay |
|---|---|---|
| p53 | 93.8% | 97.3% |
| c-myc | 93.8% | 94.6% |
| NY-ESO-1 | 90.0% | 93.3% |
| BRCA2 | 90.0% | 94.6% |
| HER2 | 91.3% | 95.9% |
| MUC1 | 92.5% | 95.9% |
| Panel (of 6 Ags) | 71.3% | 78.4% |

It can be seen that by using several points on the antigen titration curve, both a higher sensitivity and specificity were obtained compared with a single point measurement.

Example 6

Potential Reasons for Higher Sensitivity and Specificity with Antigen Titration Assay Without being bound by theory, the applicant considers there are a number of reasons for the observed higher specificity and sensitivity in an assay where the antigen is titrated.

Figure 11:
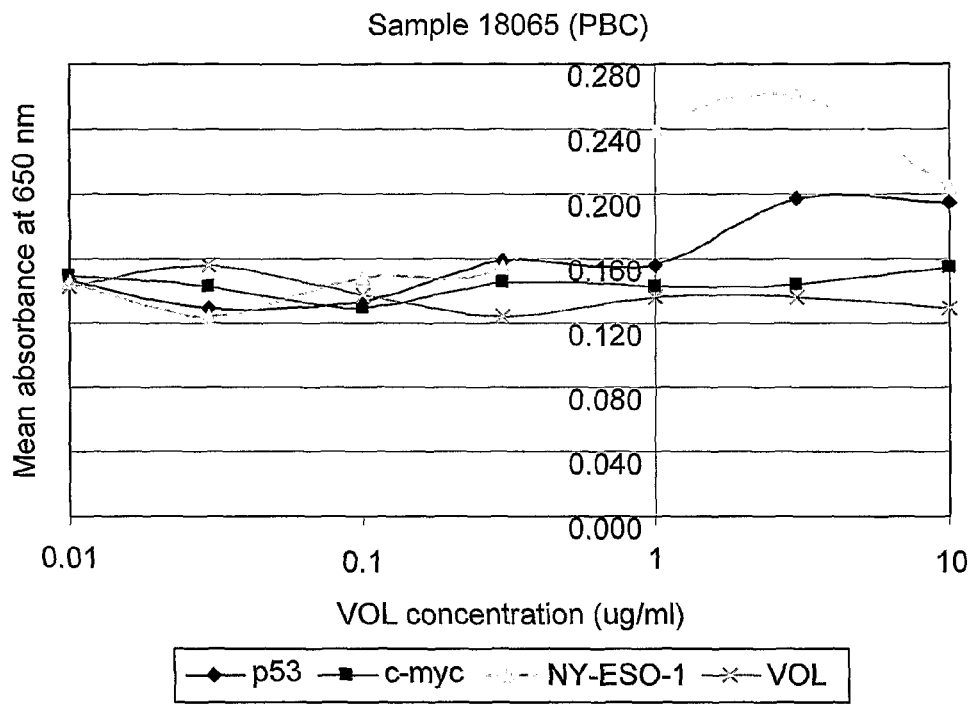
FIG. 11 illustrates the results of auto-antibody analysis from a patient with primary breast cancer using the antigen titration assay of the invention with respect to antigens p53, c-myc and NY-ESO-1 and the control expression products of the "empty" vector VOL.

(i) FIG. 11 shows the results of AAb analysis of serum from a patient with primary breast cancer (PCB) using antigens p53, c-myc and NY-ESO-1 at varying concentration. These results demonstrate that in some cases the titration curve dips at high antigen levels (NY-ESO-1 curve). This is a commonly observed phenomenon in immunochemistry. If a single point measurement at 10 µg/ml were used, this patient would have been classified as negative with respect to NY-ESO-1 autoantibodies when in fact there is clearly a positive response.

Figure 12:
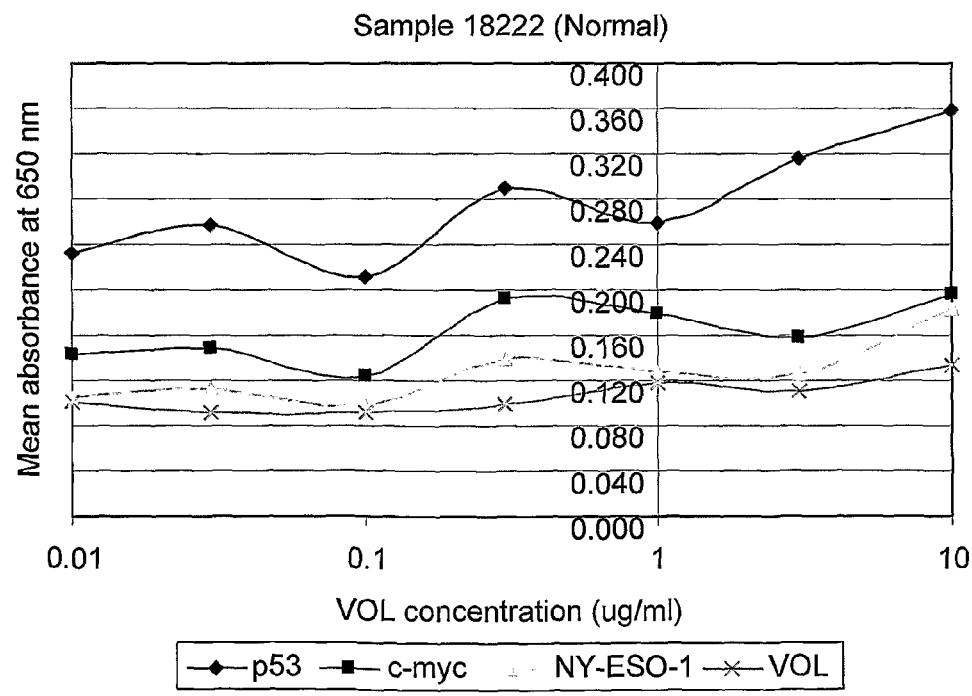
FIG. 12 illustrates the results of a repetition of the assay shown in FIG. 11 but with serum from a normal individual.

(ii) FIG. 12 shows the analysis of serum from a normal individual, also using titrated antigen p53, c-myc and NY-ESO-1. This figure demonstrates an affect which the applicants have observed in approximately 10% of assays in which the baseline of the antigen measurement (in this case p53) is shifted to a level above that of the negative control (VOL). This produces a falsely high reading. This type of result is easily identifiable with the titration assay, but would be invisible in a set of single point assays. This would result in reduced specificity due to these false positives (see Table 5).

Figure 13:
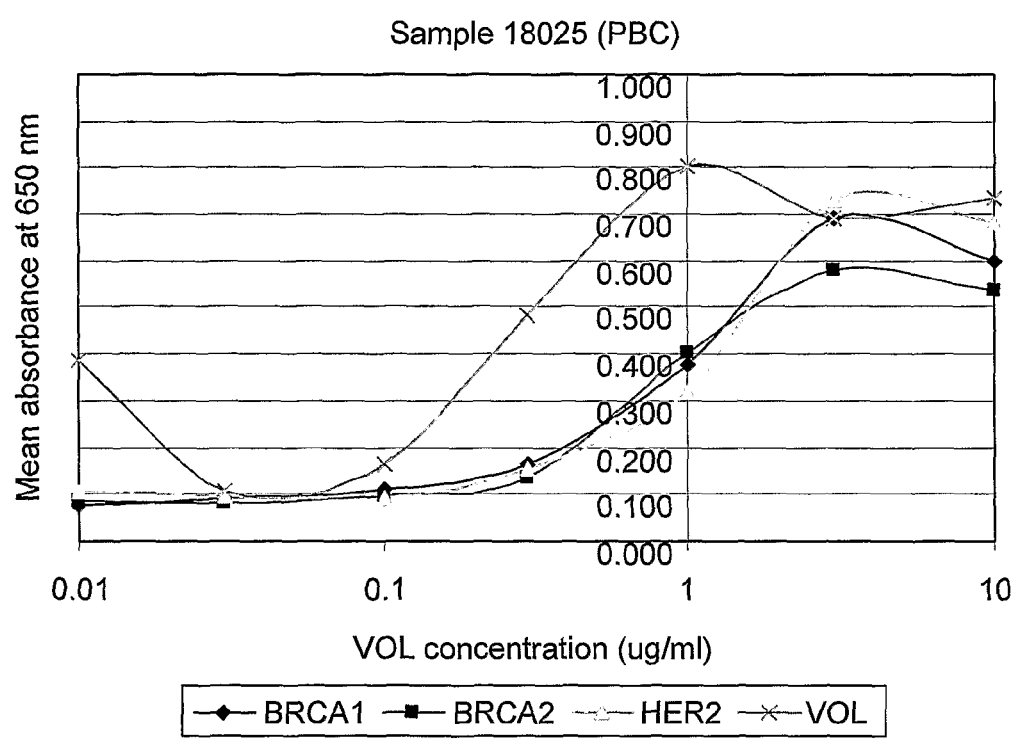
FIG. 13 illustrates further results obtained using the antigen titration assay of the invention on a patient with primary breast cancer but who also shows an antibody response to biotin.

(iii) As discussed in Example 4, the antigens that are used in the Titration AAb Assay have a biotin tag that can be used in purification of the protein. However, it is known that approximately 10% of the population produce an antibody response to biotin, which is a vitamin. FIG. 13 demonstrates an anti-biotin response in a patient with PBC. This response can be clearly-identified using the titration assay as a strong antibody response against the negative control, VOL (which is also biotinylated). These individuals must be regarded as unassessible with the assay in this format. However, if a single point assay were used, the anti-biotin responders could not be distinguished from true responses.

Example 7

Demonstration of Increased Sensitivity of Antigen Titration Compared with Serum Titration AAb measurements were performed in two ways in two quite separate experiments. The first was using the standard format in which the plate was coated with antigen in a semi-log titration from 10 µg/ml down to 0.01 µg/ml. After blocking, serum was added at a dilution of 1 in 100. In the second, the plates were coated with antigen at a concentration of 3 µg/ml and after blocking, serum was added in a semi-log titration range from a dilution of 1 in 10 down to 1 in 10,000. The methods for the remainder of the assays were identical. Two pools of serum known to be positive for p53 and c-myc were assayed along with 8 sera from women with PBC and 10 sera from normal individuals. The results are shown in table 6 below.

TABLE 6

Sensitivity of AAb assays involving titration of antigen compared with those involving titration of serum.

| PBC | Antigen p53 | Serum p53 | Antigen c-myc | Serum c-myc | Antigen BRCA2 | Serum BRCA2 |
|---|---|---|---|---|---|---|
| p53 +ve | ++ | +++ | ++ | ++ | − | − |
| c-myc +ve | − | − | + | + | − | − |
| 17179 | +++ | +++ | +++ | +++ | ++ | + |
| 19451 | + | ++ | − | − | − | − |
| 18237 | ++ | ++ | ++ | + | + | − |
| 18489 | − | − | − | − | + | − |
| 19510 | − | − | − | − | − | − |
| 19190 | + | − | − | − | + | ++ |
| 18610 | + | − | + | + | − | − |
| 18458 | + | − | + | − | − | − |
| positivity | 70% | 40% | 60% | 50% | 40% | 20% |

It can be seen that the assay format involving titration of antigen is more sensitive than the format involving titration of serum. Samples that were strongly positive were detected by both formats, however weak positives in the antigen titration assay were generally not detected in the serum titration assay.

Figure 14:
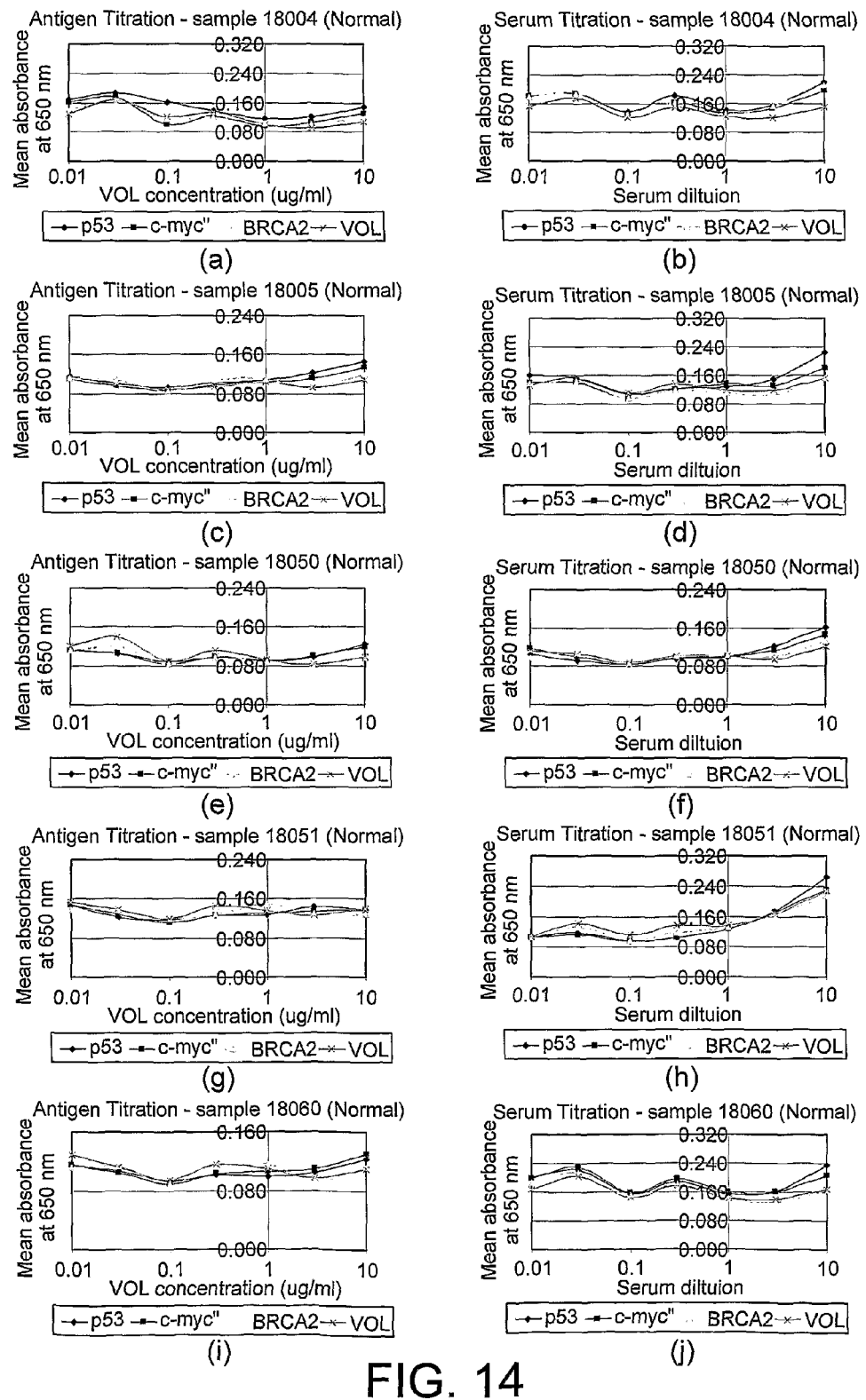
FIG. 14 illustrates the results of experimental comparison on normal samples between an auto-antibody detection assay when the antigen is titrated in accordance with the invention and an auto-antibody detection assay in which the antigen amount remains constant but the serum is titrated.
Figure 14:
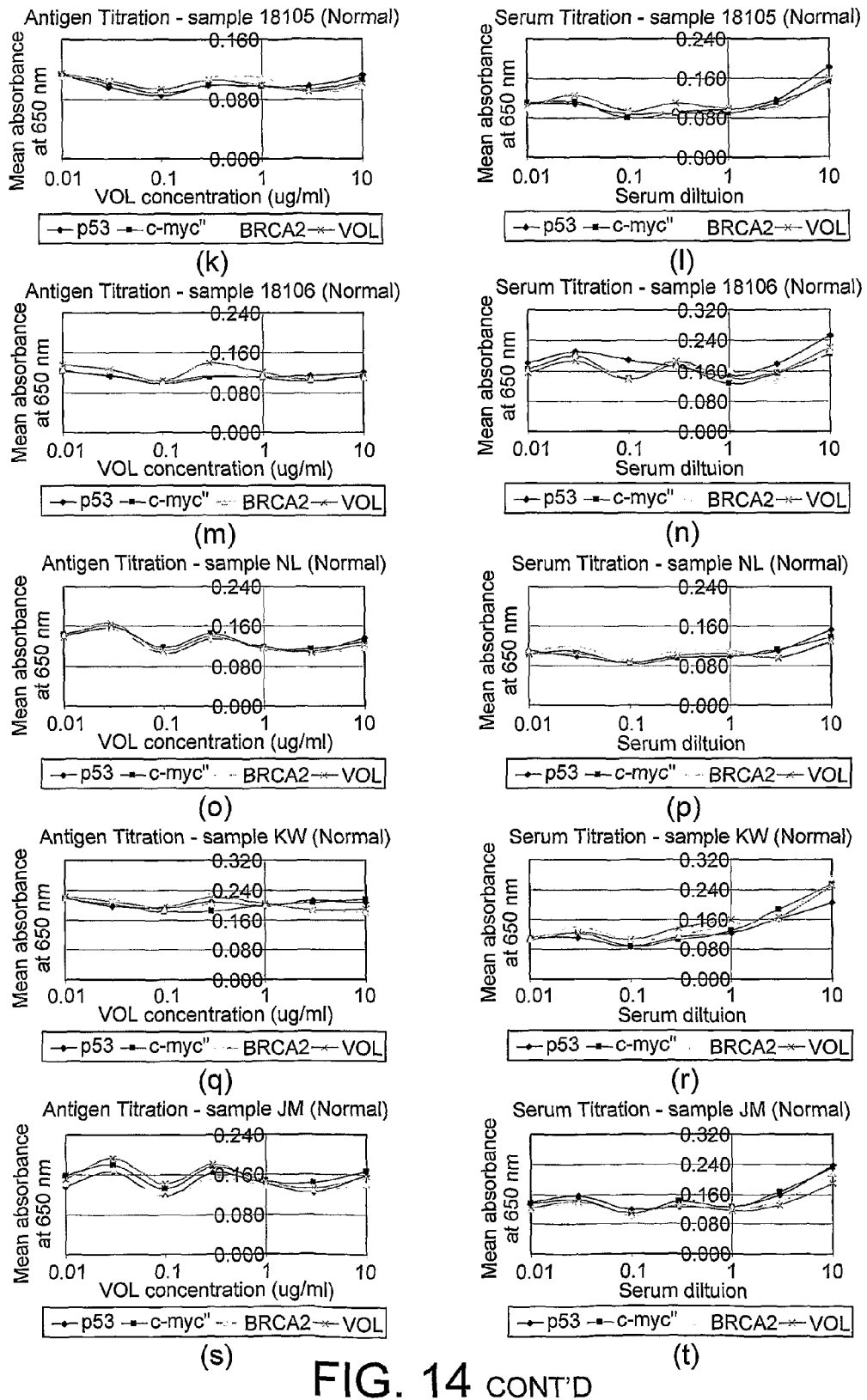

The lower sensitivity demonstrated by the serum titration format is due to the inherent non-specific binding of serum at high concentration. This causes a level of binding to the proteins even in normal samples (see FIG. 14), which elevates the normal cut-off value with subsequent reduction in sensitivity. The specificity was also reduced in the serum titration format (BRCA2=90%) compared with the antigen titration format (BRCA2=100%).

Figure 15A:
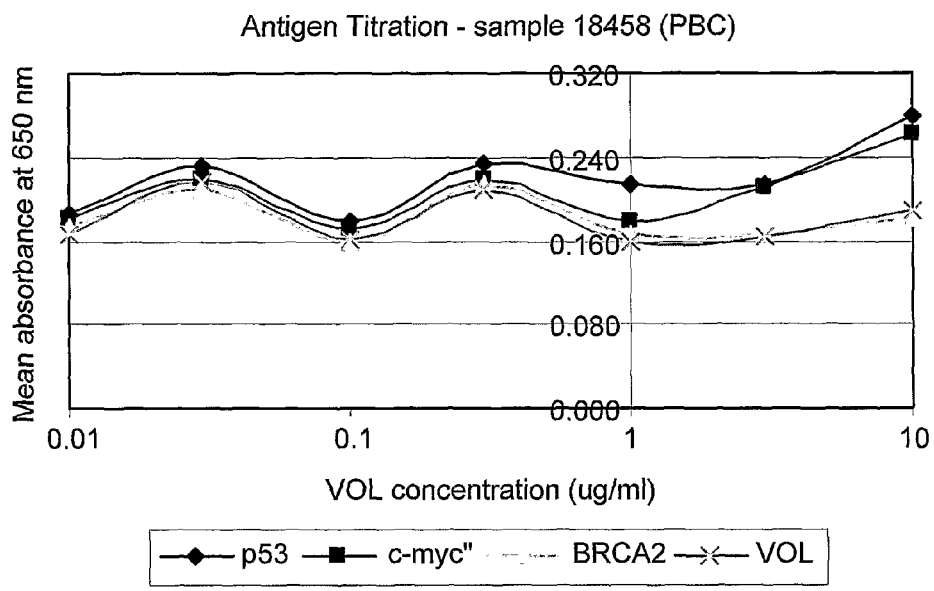
FIG. 15 illustrates the results of an experimental comparison, on a sample from a patient with primary breast cancer, between an auto-antibody detection assay when the antigen is titrated in accordance with the invention and an auto-antibody detection assay when the antigen amount remains constant but the serum is titrated.
Figure 15B:
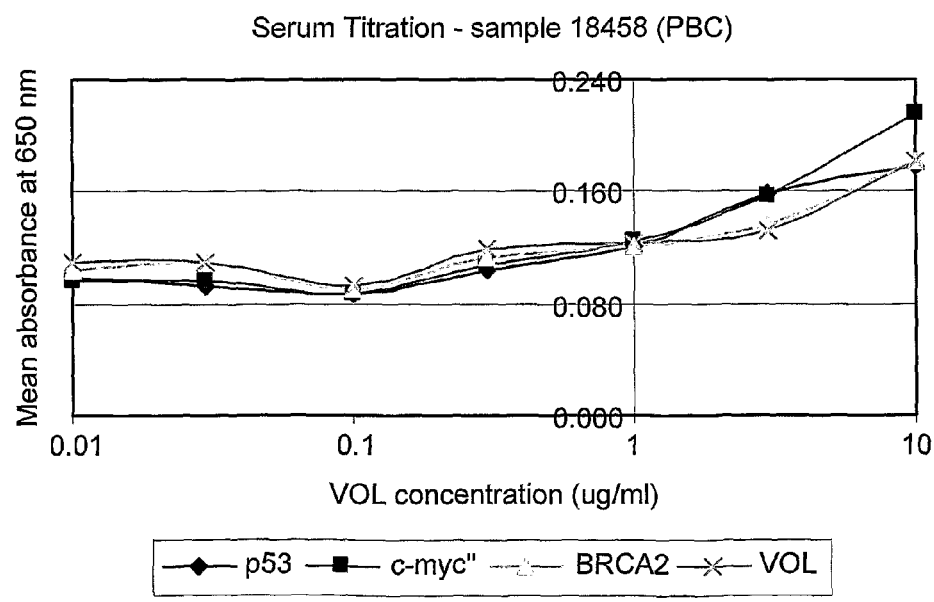

FIG. 15 reflects the experiments shown in FIG. 4 but with serum from a patient with primary breast cancer. The patient was found to be positive for auto-antibodies against p53 and c-myc but negative for auto-antibodies against BRCA2 when the antigen titration method of the invention was used. However, when auto-antibodies were measured within a serum titration range no auto-antibodies were detected (see Table 6). This is due to the non-specific binding exhibited by serum at high concentrations (demonstrated by the high level of binding to the negative control protein (VOL)) which masks signals due to specific auto-antibody binding. The consequence is that with serum dilution the assay could designate a patient with primary breast cancer, negative. Since sensitivity=True positives/True positives+false negatives this has the effect of increasing the denominator and therefore decreasing the sensitivity.

In Summary, the applicants have shown that Antigen Titration Autoantibody assays are more sensitive and specific than measuring autoantibody reactivity at a single antigen concentration. This is because the antigen titration provides the scope to detect both low abundance, low affinity antibodies at high antigen concentrations as well as high abundance antibodies which would otherwise hook at high antigen concentration but bind maximally further down the titration curve. It also allows discrimination of non-assessable assays from true results, which is not possible with single point measurement. It is believed an antigen titration AAb assays are more sensitive than mere titration of serum because the high level of non-specific binding observed with serum at high concentration raises normal cut-off levels thereby decreasing sensitivity.

The invention claimed is:

1. A method of detecting a disease state or disease susceptibility in a mammalian subject, comprising detecting an antibody in a bodily fluid test sample from the subject wherein the antibody is a biological marker of a disease state or disease susceptibility and wherein it is not known whether the test sample comprises the antibody, the method comprising:
 (a) contacting the test sample with a plurality of different amounts of an antigen specific for the antibody,
 (b) detecting the amount of specific binding between the antibody and the antigen,
 (c) plotting or calculating a curve of the amount of specific binding versus the amount of antigen for each amount of antigen used in step (a), and
 (d) comparing the curve of the test sample with a control sample curve,
 wherein a difference in the test sample curve when compared with the control sample curve indicates the presence of a disease state or susceptibility in the subject.

2. The method of claim 1 wherein the curves are based upon the collective values of the amount of specific binding for the antigen amounts.

3. The method of claim 1 wherein a test sample curve having a generally S-shaped or sigmoidal curve indicates a disease state or susceptibility in the subject.

4. The method of claim 1 wherein the antibody is an autoantibody specific for a tumour marker protein.

5. The method of claim 4 wherein the antigen is a tumour marker protein or an antigenic fragment or epitope thereof.

6. The method of claim 5 wherein the tumour marker protein is MUC1, MUC16, c-myc, EGFR, p53, ras, BRCA1, BRCA2, APC, HER2, PSA, CEA, CA19.9, NY-ESO-1, 4-5, CAGE, PSMA, PSCA, EpCam, a cytokeratin, recoverin, a kallikrein, an annexin, AFP, GRP78, CA125, mammoglobin, or raf.

7. The method of claim 4 wherein the presence or absence of the disease state or disease susceptibility provides a diagnosis or prognosis of cancer or monitors cancer.

8. The method of claim 4 wherein the presence or absence of the disease state or disease susceptibility identifies, in a population of asymptomatic human subjects, those subjects who are at increased risk of developing cancer, wherein the samples to be tested using the method are samples of bodily fluid taken from the subjects, and wherein subjects having an elevated level of autoantibodies, as compared to normal control individuals, are identified as being at risk of developing cancer.

9. The method of claim 4 wherein the presence or absence of the disease state or disease susceptibility detects early neoplastic or early carcinogenic change in an asymptomatic human subject, wherein the sample to be tested using the method is a sample of bodily fluid taken from the subject, and wherein the presence of an elevated level of autoantibodies, as compared to normal control individuals, is taken as an indication of early neoplastic or early carcinogenic change in the subject.

10. The method of claim 4 wherein the presence or absence of the disease state or disease susceptibility, in a population of asymptomatic human subjects, identifies those subjects who have developed a cancer, wherein the samples to be tested using the method are samples of bodily fluid taken from the subjects, and wherein subjects having an elevated level of autoantibodies, as compared to normal control individuals, are diagnosed as having a cancer.

11. The method of claim 4 wherein the presence or absence of the disease state or disease susceptibility in a population of symptomatic human subjects identifies those subjects who have developed a cancer, wherein the samples to be tested using the method are samples of bodily fluid taken from the subjects, and wherein subjects having an elevated level of autoantibodies, as compared to normal control individuals, are diagnosed as having a cancer.

12. The method of claim 4 wherein the presence or absence of the disease state or disease susceptibility monitors the progress of cancer or other neoplastic disease in a patient, wherein the sample to be tested using the method is a sample of bodily fluid taken from a human patient, and wherein the presence of an elevated level of autoantibodies, as compared to a normal control, is taken as an indication of the presence of cancer in the patient.

13. The method of claim 4 wherein the presence or absence of the disease state or disease susceptibility detects recurrent disease in a human patient previously diagnosed as having cancer, which patient has undergone anti-cancer treatment to reduce the amount of cancer present, wherein the sample to be tested using the method is a sample of bodily fluid taken from the patient, and wherein the presence of an increased level of autoantibodies in the patient, as compared to a normal control, is taken as an indication that disease has recurred.

14. The method of claim 4 wherein the presence or absence of the disease state or disease susceptibility provides an assessment of prognosis from cancer, wherein the sample to be tested using the method is a sample of bodily fluid taken from a human patient, and wherein the presence of an elevated level of autoantibodies, as compared to a normal control, is taken as an indication of the prognosis of the patient from their cancer.

15. The method of claim 4 wherein the presence or absence of the disease state or disease susceptibility predicts response to anti-cancer treatment, wherein the sample to be tested using the method is a sample of bodily fluid taken from a human patient, and wherein comparison of the level of autoantibodies in said patient with a previously established relationship between levels of autoantibodies and likely outcome of treatment is used to provide an indication of whether the patient will respond to such anti-cancer treatment.

16. The method of claim 15 wherein the anti-cancer treatment is vaccination, anti-growth factor or signal transduction therapy, radiotherapy, endocrine therapy, human antibody therapy or chemotherapy.

17. The method of claim 4 wherein the presence or absence of the disease state or disease susceptibility monitors the response of a human cancer patient to anti-cancer treatment, wherein the sample to be tested using the method is a sample of bodily fluid taken from the patient, and wherein a change in the level of autoantibodies after treatment is taken as an indication of whether or not the patient has responded to the treatment.

18. The method of claim 17 wherein the treatment is vaccination, anti-growth factor or signal transduction therapy, radiotherapy, endocrine therapy, human antibody therapy or chemotherapy and a change in the level of autoantibodies after treatment is taken as an indication that the patient has responded positively to the treatment.

19. A method of identifying an anti-cancer treatment for a human patient, comprising detecting one or more autoantibodies specific for tumour marker proteins in a bodily fluid test sample from the patient and wherein it is not known whether the test sample comprises the autoantibodies, the method comprising:
  (a) contacting the test sample with a panel of a plurality of different amounts of two or more antigens each corresponding to a different tumour marker protein specific for an autoantibody,
  (b) detecting the amount of specific binding between the autoantibody and each antigen,
  (c) plotting or calculating a curve of the amount of the specific binding versus the amount of antigen for each amount of each antigen used in step (a), and
  (d) determining the relative strength of the patient's immune response to each of the different tumour marker proteins, wherein the tumour marker protein or proteins identified as eliciting the strongest immune response or strong responses in the patient is or are selected to form the basis of an anti-cancer treatment for use in the patient.

20. The method of claim 19 wherein the anti-cancer treatment is vaccination and the tumour marker protein or proteins identified as eliciting the strongest immune response or strong responses in the patient is or are selected to form the basis of an anti-cancer vaccine for use in the patient.

21. A method of detecting an antibody in a test sample comprising a bodily fluid from a mammalian subject wherein said antibody is a biological marker of a disease state or disease susceptibility and wherein it is not known whether the test sample comprises the antibody, the method comprising:
  a) contacting the test sample with a plurality of different amounts of an antigen specific for said antibody,
  b) detecting the amount of specific binding between said antibody and said antigen and
  c) plotting or calculating a curve of the amount of said specific binding versus the amount of antigen for each amount of antigen used in step (a) and
  d. comparing the curve to a control curve,
  wherein a difference between the test sample curve and the control curve indicates the presence of antibody in the test sample.

22. The method of claim 21 wherein the presence in the test sample of antibody reactive with the antigen used in the assay is indicated by a generally S-shaped or sigmoidal curve.

23. The method of claim 21 wherein the antibody is an autoantibody specific for a tumour marker protein.

24. The method of claim 21 wherein the antigen is a tumour marker protein or an antigenic fragment or epitope thereof.

25. The method of claim 24 wherein the tumour marker protein is MUC1, MUC16, c-myc, EGFR, p53, ras, BRCA1, BRCA2, APC, HER2, PSA, CEA, CA19.9, NY-ESO-1, 4-5, CAGE, PSMA, PSCA, EpCam, a cytokeratin, recoverin, a kallikrein, an annexin, AFP, GRP78, CA125, mammoglobin, or raf.

26. The method of claim 21 wherein the presence or absence of the disease state or disease susceptibility provides a diagnosis or prognosis of cancer or monitors cancer.

27. The method of claim 21 wherein, in a population of asymptomatic human subjects, those subjects having an elevated level of specific binding between autoantibody and antigen at each different antigen concentration, as compared to normal control individuals, are identified as being at increased risk of developing cancer.

28. The method of claim 21 wherein the antigen is a naturally occurring protein or polypeptide, a recombinant protein or polynucleotide, a synthetic protein or polypeptide, synthetic peptide, peptide mimetic, polysaccharide or nucleic acid.

29. A method of detecting a disease state or disease susceptibility in a mammalian subject, comprising:
  (a) contacting a test sample from the subject with a plurality of different amounts of an antigen, wherein it is not known whether the test sample comprises autoantibody and wherein the antigen is a tumor marker protein or an antigenic fragment or epitope thereof, and wherein autoantibody in the test sample binds to the antigen,
  (b) detecting the amount of specific binding between autoantibody and each amount of antigen,
  (c) plotting or calculating a curve of the amount of specific binding versus the amount of antigen for each amount of antigen, and
  (d) comparing the curve of the test sample with a curve of a control sample at the same amounts of the same antigen,
  wherein a difference in test sample curve, when compared with control, indicates disease state or susceptibility in the subject.

30. The method of claim 29 wherein the test sample curve is generally S-shaped or sigmoidally shaped.

31. The method of claim 1 wherein an increased amount of specific binding, when compared to a normal control having the same dilutions, indicates the presence of disease state or susceptibility.

32. The method of claim 19 wherein an increased amount of specific binding, when compared to a normal control having the same dilutions, indicates the presence of disease state or susceptibility.

33. The method of claim 21 wherein an increased amount of specific binding, when compared to a normal control having the same dilutions, indicates the presence of disease state or susceptibility.

34. The method of claim 29 wherein an increased amount of specific binding, when compared to a normal control having the same dilutions, indicates the presence of disease state or susceptibility.

* * * * *